(12) United States Patent
Osborne, Jr.

(10) Patent No.: US 12,114,812 B2
(45) Date of Patent: *Oct. 15, 2024

(54) DISPENSING AND MONITORING SYSTEMS AND METHODS

(71) Applicant: Valve Solutions, Inc., Alpharetta, GA (US)

(72) Inventor: Charles Agnew Osborne, Jr., Cumming, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/242,715

(22) Filed: Sep. 6, 2023

(65) Prior Publication Data

US 2023/0404333 A1 Dec. 21, 2023

Related U.S. Application Data

(63) Continuation of application No. 16/732,013, filed on Dec. 31, 2019, now Pat. No. 11,779,167.
(Continued)

(51) Int. Cl.
*A47K 10/36* (2006.01)
*A47K 5/12* (2006.01)
(Continued)

(52) U.S. Cl.
CPC ............ *A47K 10/36* (2013.01); *A47K 5/1217* (2013.01); *A47K 10/3625* (2013.01);
(Continued)

(58) Field of Classification Search
CPC .. G08B 21/245; G16H 10/20; A47K 10/3625; A47K 2010/3668
See application file for complete search history.

(56) References Cited

U.S. PATENT DOCUMENTS 5,610,589 A  3/1997 Evans et al.
5,808,553 A  9/1998 Cunningham
(Continued)

FOREIGN PATENT DOCUMENTS

KR  10-0990823 B1  10/2010
WO  WO2004/086287 A2  10/2004
(Continued)

OTHER PUBLICATIONS

Adafruit Pir Motion Sensor; "How PIRs Work"; https://learn.adafruit.com/pir-passive-infrared-proximity-motion-sensor?view=all#how-pirs-work; Jan. 28, 2014.
(Continued)

*Primary Examiner* — Timothy R Waggoner
(74) *Attorney, Agent, or Firm* — Womble Bond Dickinson (US) LLP

(57) ABSTRACT

The present disclosure is directed to systems and methods that facilitate identifying, logging, mapping, and/or tracking of the movements and/or activities of individuals throughout a facility using a plurality of dispensers are positioned at selected locations about the facility. The systems and methods further allow for capturing infrared radiation of one or more individuals within a prescribed detection range, area, or zone covered using at least one passive infrared radiation sensor. The control system of a dispenser of the plurality of dispensers can be disconnected from a power source of the dispenser when the at least one passive infrared radiation sensor does not capture infrared radiation of one or more individuals within the prescribed detection range, area, or zone. Other aspects also are described.

30 Claims, 16 Drawing Sheets

Related U.S. Application Data

(60) Provisional application No. 62/932,220, filed on Nov. 7, 2019, provisional application No. 62/787,622, filed on Jan. 2, 2019.

(51) Int. Cl.
| | | |
|---|---|---|
| *A47K 10/32* | (2006.01) | |
| *G06K 19/077* | (2006.01) | |
| *G16H 40/20* | (2018.01) | |
| *H04W 4/029* | (2018.01) | |
| *H04W 52/02* | (2009.01) | |

(52) U.S. Cl.
CPC ....... *G06K 19/07758* (2013.01); *G16H 40/20* (2018.01); *H04W 4/029* (2018.02); *H04W 52/0212* (2013.01); *A47K 2010/3226* (2013.01); *A47K 2010/3668* (2013.01)

(56) References Cited

U.S. PATENT DOCUMENTS

| | | |
|---|---|---|
| 5,864,894 A | 2/1999 | Fedele |
| 5,900,801 A | 5/1999 | Heagle et al. |
| 5,939,974 A | 8/1999 | Heagle et al. |
| 5,945,910 A | 8/1999 | Gorra |
| 6,147,607 A | 11/2000 | Lynn |
| 6,236,317 B1 | 5/2001 | Cohen et al. |
| 6,236,953 B1 | 5/2001 | Segal |
| 6,278,372 B1 | 8/2001 | Velasco et al. |
| 6,346,886 B1 | 2/2002 | DeLaHuerga |
| 6,347,414 B2 | 2/2002 | Contadini et al. |
| 6,645,435 B2 | 11/2003 | Dawson et al. |
| 6,882,278 B2 | 4/2005 | Winings et al. |
| 6,883,563 B2 | 4/2005 | Smith |
| 6,975,231 B2 | 12/2005 | Lane et al. |
| 7,213,782 B2 | 5/2007 | Osborne et al. |
| 7,312,782 B2 | 5/2007 | Osborne et al. |
| 7,242,307 B1 | 7/2007 | LeBlond et al. |
| 7,271,719 B2 | 9/2007 | Ku et al. |
| 7,271,728 B2 | 9/2007 | Taylor et al. |
| 7,293,645 B2 | 11/2007 | Harper et al. |
| 7,315,245 B2 | 1/2008 | Lynn et al. |
| 7,370,824 B1 | 5/2008 | Osborne |
| 7,372,367 B2 | 5/2008 | Lane et al. |
| 7,375,640 B1 | 5/2008 | Plost |
| 7,408,470 B2 | 8/2008 | Wildman et al. |
| 7,423,533 B1 | 9/2008 | LeBlond et al. |
| 7,425,900 B2 | 9/2008 | Lynn et al. |
| 7,460,013 B1 | 12/2008 | Osborne |
| 7,477,148 B2 | 1/2009 | Lynn et al. |
| 7,598,854 B2 | 10/2009 | Wong |
| 7,659,824 B2 | 2/2010 | Prodanovich et al. |
| 7,726,599 B2 | 6/2010 | Lewis et al. |
| 7,755,494 B2 | 7/2010 | Melker et al. |
| 7,770,782 B2 | 8/2010 | Sahud |
| 7,779,059 B2 | 8/2010 | Bourland et al. |
| 7,782,214 B1 | 8/2010 | Lynn |
| 7,812,730 B2 | 10/2010 | Wildman et al. |
| 7,818,083 B2 | 10/2010 | Glenn et al. |
| 7,825,812 B2 | 11/2010 | Ogrin et al. |
| 7,855,651 B2 | 12/2010 | LeBlond et al. |
| 7,893,842 B2 | 2/2011 | Deutsch |
| 7,898,407 B2 | 3/2011 | Hufton et al. |
| 7,952,484 B2 | 5/2011 | Lynn |
| 7,978,083 B2 | 7/2011 | Melker et al. |
| 8,085,155 B2 | 12/2011 | Prodanovich et al. |
| 8,094,029 B2 | 1/2012 | Ortiz et al. |
| 8,146,613 B2 | 4/2012 | Barnhill et al. |
| 8,160,742 B2 | 4/2012 | Goerg et al. |
| 8,164,439 B2 | 4/2012 | Dempsey et al. |
| 8,169,327 B2 | 5/2012 | Lynn |
| 8,196,810 B2 | 6/2012 | Sahud |
| 8,212,653 B1 | 7/2012 | Goldstein et al. |
| 8,229,185 B2 | 7/2012 | Ennis et al. |
| 8,237,558 B2 | 8/2012 | Seyed Momen et al. |
| 8,249,295 B2 | 8/2012 | Johnson |
| 8,250,657 B1 | 8/2012 | Nachenberg et al. |
| 8,264,343 B2 | 9/2012 | Snodgrass |
| 8,294,584 B2 | 10/2012 | Plost |
| 8,294,585 B2 | 10/2012 | Barnhill |
| 8,299,896 B2 | 10/2012 | Mahmoodi et al. |
| 8,334,777 B2 | 12/2012 | Wilson et al. |
| 8,344,893 B1 | 1/2013 | Drammeh |
| 8,350,706 B2 | 1/2013 | Wegelin et al. |
| 8,368,544 B2 | 2/2013 | Wildman et al. |
| 8,377,229 B2 | 2/2013 | Barnhill et al. |
| 8,395,515 B2 | 3/2013 | Tokhtuev et al. |
| 8,400,309 B2 | 3/2013 | Glenn et al. |
| 8,405,503 B2 | 3/2013 | Wong |
| 8,427,323 B2 | 4/2013 | Alper et al. |
| 8,448,848 B2 | 5/2013 | Sahud |
| 8,482,406 B2 | 7/2013 | Snograss |
| 8,498,851 B2 | 7/2013 | Ehrnsperger et al. |
| 8,502,680 B2 | 8/2013 | Tokhtuev et al. |
| 8,502,681 B2 | 8/2013 | Bolling et al. |
| 8,525,666 B2 | 9/2013 | Melker et al. |
| 8,547,220 B1 | 10/2013 | Dempsey et al. |
| 8,558,660 B2 | 10/2013 | Nix et al. |
| 8,558,701 B2 | 10/2013 | Wegelin et al. |
| 8,564,431 B2 | 10/2013 | Snodgrass |
| 8,566,478 B2 | 10/2013 | Ota et al. |
| 8,566,932 B1 | 10/2013 | Hotta et al. |
| 8,587,437 B2 | 11/2013 | Kyle et al. |
| 8,598,996 B2 | 12/2013 | Wildman et al. |
| 8,633,816 B2 | 1/2014 | Snodgrass et al. |
| 8,640,275 B2 | 2/2014 | Lawson et al. |
| 8,673,210 B2 | 3/2014 | Deshays |
| 8,674,840 B2 | 3/2014 | Snodgrass |
| 8,698,637 B2 | 4/2014 | Raichman |
| 8,717,177 B2 | 5/2014 | Cartner |
| 8,742,932 B2 | 6/2014 | Casares |
| 8,744,623 B2 | 6/2014 | Drake et al. |
| 8,746,558 B2 | 6/2014 | Healy et al. |
| 8,800,415 B2 | 8/2014 | Osborne |
| 8,922,378 B2 | 12/2014 | Raccio |
| 9,117,361 B1 | 8/2015 | Hennigan et al. |
| 9,741,233 B2 | 8/2017 | Laufer et al. |
| 9,756,992 B2 | 9/2017 | Osborne |
| 9,907,441 B2 | 3/2018 | Osborne et al. |
| 9,918,598 B2 | 3/2018 | Osborne |
| 9,972,193 B2 | 5/2018 | Laufer et al. |
| 10,105,020 B2 | 10/2018 | Carper et al. |
| 10,123,665 B2 | 11/2018 | Osborne, Jr. |
| 10,136,769 B2 | 11/2018 | Osborne, Jr. et al. |
| 10,213,068 B2 | 2/2019 | Diamond |
| 10,441,117 B2 | 10/2019 | Osborne, Jr. |
| 10,446,013 B2 | 10/2019 | Laufer et al. |
| 10,602,887 B2 | 3/2020 | Troutman |
| 10,610,064 B2 | 4/2020 | Osborne |
| 10,660,486 B2 | 5/2020 | Osborne, Jr. |
| 10,720,042 B2 | 7/2020 | Laufer et al. |
| 10,835,086 B2 | 11/2020 | Osborne, Jr. |
| 11,071,415 B2 | 7/2021 | Osborne, Jr. |
| 11,109,722 B2 | 9/2021 | Osborne, Jr. |
| 11,142,419 B2 | 10/2021 | Osborne, Jr. |
| 11,154,166 B2 | 10/2021 | Osborne, Jr. |
| 11,246,460 B2 | 2/2022 | Osborne, Jr. |
| 11,282,370 B2 | 3/2022 | Laufer et al. |
| 11,478,111 B2 | 10/2022 | Osborne, Jr. |
| 11,612,278 B2 | 3/2023 | Osborne, Jr. |
| 11,612,279 B2 * | 3/2023 | Osborne, Jr. ..... H04W 52/0212 242/563 |
| 11,655,117 B2 | 5/2023 | Osborne, Jr. |
| 11,715,365 B2 | 8/2023 | Laufer et al. |
| 11,730,324 B2 | 8/2023 | Osborne, Jr. |
| 11,779,167 B2 * | 10/2023 | Osborne, Jr. ........ A47K 5/1217 221/33 |
| 11,910,964 B2 * | 2/2024 | Osborne, Jr. ..... H04W 52/0212 |
| 2002/0135486 A1 | 9/2002 | Brohagen et al. |
| 2003/0019536 A1 | 1/2003 | Smith |
| 2005/0167541 A1 | 8/2005 | Osborne |
| 2005/0231373 A1 | 10/2005 | Lynn et al. |
| 2006/0173576 A1 | 8/2006 | Goerg et al. |
| 2007/0020212 A1 | 1/2007 | Bernal et al. |

(56) References Cited

U.S. PATENT DOCUMENTS

| | | |
|---|---|---|
| 2007/0096930 A1 | 5/2007 | Cardoso |
| 2007/0229288 A1 | 10/2007 | Ogrin et al. |
| 2007/0247316 A1 | 10/2007 | Wildman et al. |
| 2008/0001763 A1 | 1/2008 | Raja et al. |
| 2008/0087719 A1 | 4/2008 | Sahud |
| 2008/0100441 A1 | 5/2008 | Prodanovich et al. |
| 2008/0126126 A1 | 5/2008 | Ballai |
| 2008/0136649 A1 | 6/2008 | Van De Hey |
| 2008/0303658 A1 | 12/2008 | Melker et al. |
| 2009/0091458 A1 | 4/2009 | Deutsch |
| 2009/0189759 A1 | 7/2009 | Wildman et al. |
| 2009/0195385 A1 | 8/2009 | Huang et al. |
| 2009/0224907 A1 | 9/2009 | Sinha et al. |
| 2009/0224924 A1 | 9/2009 | Thorp |
| 2009/0267776 A1 | 10/2009 | Glenn |
| 2009/0272405 A1 | 11/2009 | Barnhill et al. |
| 2009/0273477 A1 | 11/2009 | Barnhill |
| 2010/0073162 A1 | 3/2010 | Johnson et al. |
| 2010/0090837 A1 | 4/2010 | Jung et al. |
| 2010/0094581 A1 | 4/2010 | Cagle |
| 2010/0117823 A1 | 5/2010 | Wholtjen |
| 2010/0155416 A1 | 6/2010 | Johnson |
| 2010/0164728 A1 | 7/2010 | Plost |
| 2010/0231385 A1 | 9/2010 | Melker et al. |
| 2010/0238021 A1 | 9/2010 | Harris |
| 2010/0265059 A1 | 10/2010 | Melker et al. |
| 2010/0328076 A1 | 12/2010 | Kyle et al. |
| 2011/0018998 A1 | 1/2011 | Guzik |
| 2011/0057799 A1 | 3/2011 | Taneff |
| 2011/0121974 A1 | 5/2011 | Tenarvitz et al. |
| 2011/0125524 A1 | 5/2011 | Tenarvitz et al. |
| 2011/0169643 A1 | 7/2011 | Cartner |
| 2011/0169645 A1 | 7/2011 | Cartner et al. |
| 2011/0169646 A1 | 7/2011 | Raichman |
| 2011/0193703 A1 | 8/2011 | Payton et al. |
| 2011/0205061 A1 | 8/2011 | Wilson et al. |
| 2011/0254682 A1 | 10/2011 | Sigrist Christensen |
| 2011/0271441 A1 | 11/2011 | Bayley et al. |
| 2011/0273298 A1 | 11/2011 | Snodgrass et al. |
| 2011/0291841 A1 | 12/2011 | Hollock et al. |
| 2011/0297830 A1 | 12/2011 | Willden |
| 2011/0316695 A1 | 12/2011 | Li et al. |
| 2011/0316701 A1 | 12/2011 | Alper et al. |
| 2011/0316703 A1 | 12/2011 | Butler et al. |
| 2012/0013470 A1 | 1/2012 | Lynn |
| 2012/0055986 A1 | 3/2012 | Sahud |
| 2012/0062382 A1 | 3/2012 | Taneff |
| 2012/0112906 A1 | 5/2012 | Borke et al. |
| 2012/0112914 A1 | 5/2012 | Wegelin et al. |
| 2012/0158419 A1 | 6/2012 | Nuthi |
| 2012/0253510 A1 | 10/2012 | Thomas et al. |
| 2012/0256742 A1 | 10/2012 | Snodgrass et al. |
| 2012/0268277 A1 | 10/2012 | Best |
| 2012/0270261 A1 | 10/2012 | Mayer et al. |
| 2012/0274468 A1 | 11/2012 | Wegelin et al. |
| 2012/0303159 A1 | 11/2012 | Drake et al. |
| 2013/0025714 A1 | 1/2013 | Hermann |
| 2013/0027199 A1 | 1/2013 | Bonner |
| 2013/0033376 A1 | 2/2013 | Seyed Momen et al. |
| 2013/0035900 A1 | 2/2013 | Purcell et al. |
| 2013/0038446 A1 | 2/2013 | Huseth et al. |
| 2013/0045685 A1 | 2/2013 | Kiani |
| 2013/0067658 A1 | 3/2013 | Loberger et al. |
| 2013/0076514 A1 | 3/2013 | Wegelin et al. |
| 2013/0113619 A1 | 5/2013 | Snodgrass |
| 2013/0120120 A1 | 5/2013 | Long et al. |
| 2013/0187779 A1 | 7/2013 | Pokrajac |
| 2013/0218583 A1 | 8/2013 | Marcolongo et al. |
| 2013/0229276 A1 | 9/2013 | Hunter |
| 2013/0234855 A1 | 9/2013 | Knighton |
| 2013/0257615 A1 | 10/2013 | Iseri et al. |
| 2013/0262034 A1 | 10/2013 | Iseri et al. |
| 2013/0268293 A1 | 10/2013 | Knudson et al. |
| 2013/0291947 A1 | 11/2013 | Chandler et al. |
| 2013/0320130 A1 | 12/2013 | Osborne |
| 2014/0009292 A1 | 1/2014 | Long et al. |
| 2014/0015670 A1 | 1/2014 | Wegelin et al. |
| 2014/0022073 A1 | 1/2014 | Balinski et al. |
| 2014/0022074 A1 | 1/2014 | Balinski et al. |
| 2014/0035744 A1 | 2/2014 | Wildman et al. |
| 2014/0046722 A1 | 2/2014 | Rosenbloom et al. |
| 2014/0049391 A1 | 2/2014 | Bolling et al. |
| 2014/0069951 A1 | 3/2014 | Schmidt et al. |
| 2014/0104062 A1 | 4/2014 | Weiner |
| 2014/0139339 A1 | 5/2014 | Jones et al. |
| 2014/0167917 A2 | 6/2014 | Wallace et al. |
| 2014/0240131 A1 | 8/2014 | Raccio |
| 2014/0300735 A1 | 10/2014 | Reibel et al. |
| 2015/0022025 A1 | 1/2015 | Lee et al. |
| 2016/0325957 A1 | 11/2016 | Borke |
| 2016/0353945 A1 | 12/2016 | Osborne |
| 2016/0353947 A1 | 12/2016 | Osborne |
| 2017/0051486 A1 | 2/2017 | Schomburg et al. |
| 2017/0112335 A1 | 4/2017 | Diamond |
| 2018/0146829 A1 | 5/2018 | Osborne |
| 2018/0170703 A1 | 6/2018 | Osborne, Jr. |
| 2018/0263435 A1 | 9/2018 | Osborne, Jr. |
| 2018/0293873 A1 | 10/2018 | Liu et al. |
| 2019/0174972 A1 | 6/2019 | Osborne, Jr. et al. |
| 2019/0350414 A1 | 11/2019 | Starkey |
| 2020/0054177 A1 | 2/2020 | Osborne, Jr. |
| 2020/0205620 A1 | 7/2020 | Osborne, Jr. |
| 2022/0151445 A1 | 5/2022 | Osborne, Jr. |
| 2023/0064043 A1 | 3/2023 | Osborne, Jr. |
| 2023/0233037 A1 | 7/2023 | Osborne, Jr. |
| 2023/0248189 A1 | 8/2023 | Osborne, Jr. |
| 2023/0249932 A1 | 8/2023 | Osborne, Jr. |

FOREIGN PATENT DOCUMENTS

| | | |
|---|---|---|
| WO | WO2010/099488 A1 | 9/2010 |
| WO | WO2013/058957 A2 | 4/2013 |
| WO | WO2018/216015 A1 | 11/2018 |

OTHER PUBLICATIONS

El-Pro-Cus; Electronics Projects Focus; "PIR Sensor—Basics & Applications"; https://www.elprocus.com/pir-sensor-basics-applications/; Oct. 2013.

Wikipedia; "Passive infrared sensor"; available as of Oct. 31, 2007 (lasted edited Feb. 2020).

Internet Archive; Wayback Machine; Wikipedia; Passive infrared sensor; https://en.wikipedia.org/wiki/Passive_infrared_sensor; https://web.archive.org/web/20071031191047/https://en.wikipedia.org/wiki/Passive_infrared_sensor; Oct. 31, 2013.

International Search Report and the Written Opinion of the International Search Authority for PCT/US2019/069128, mailed Apr. 28, 2020.

Partial Supplementary European Search Report regarding related Application No. EP19907898.1 mailed Jul. 26, 2022.

Extended European Search Report regarding related Application No. EP19907795.9 mailed Sep. 27, 2022.

U.S. Appl. No. 16/732,005, filed Dec. 31, 2019.

U.S. Appl. No. 17/368,901, filed Jul. 7, 2021.

U.S. Appl. No. 18/126,034, filed Mar. 24, 2023.

* cited by examiner

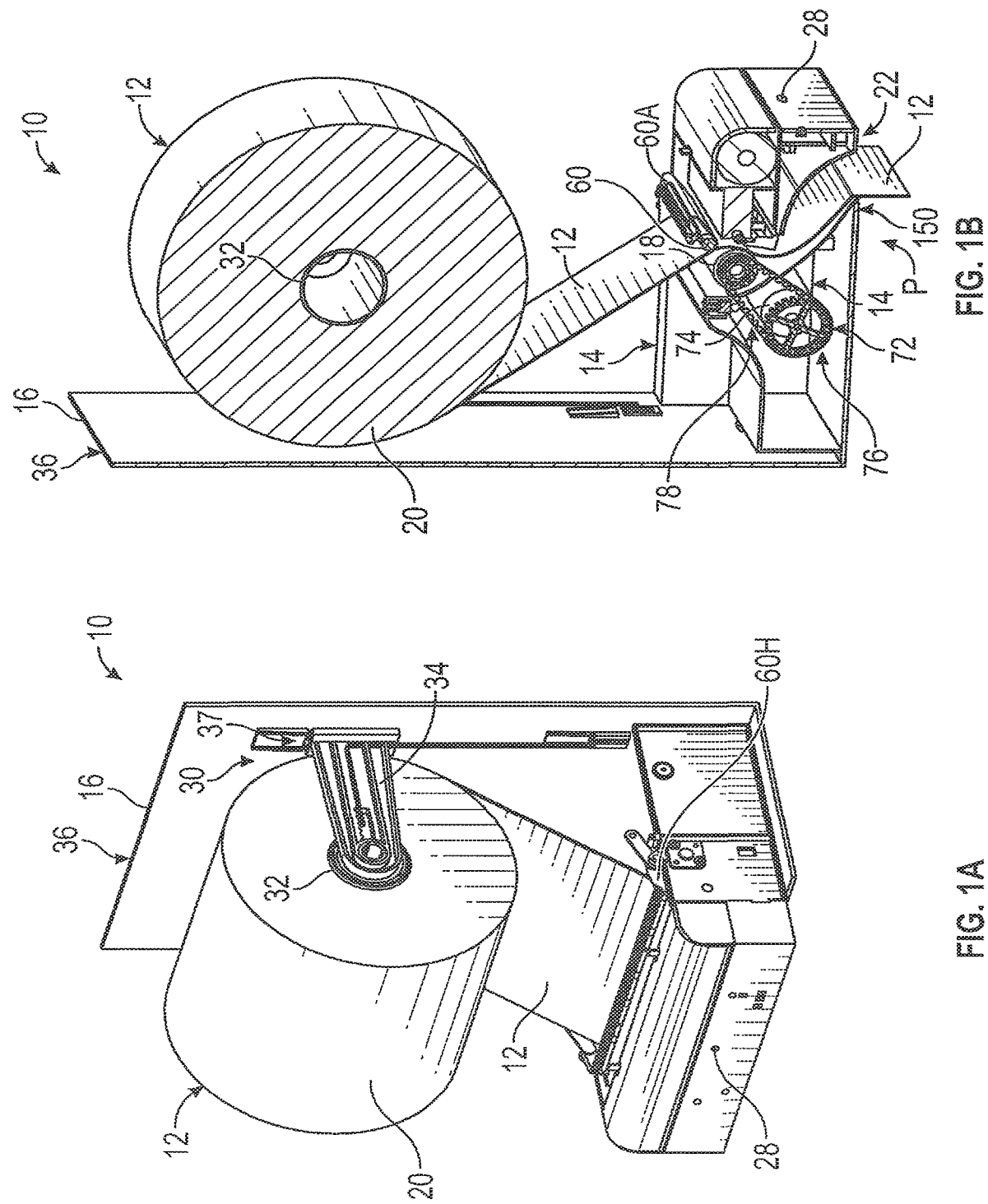

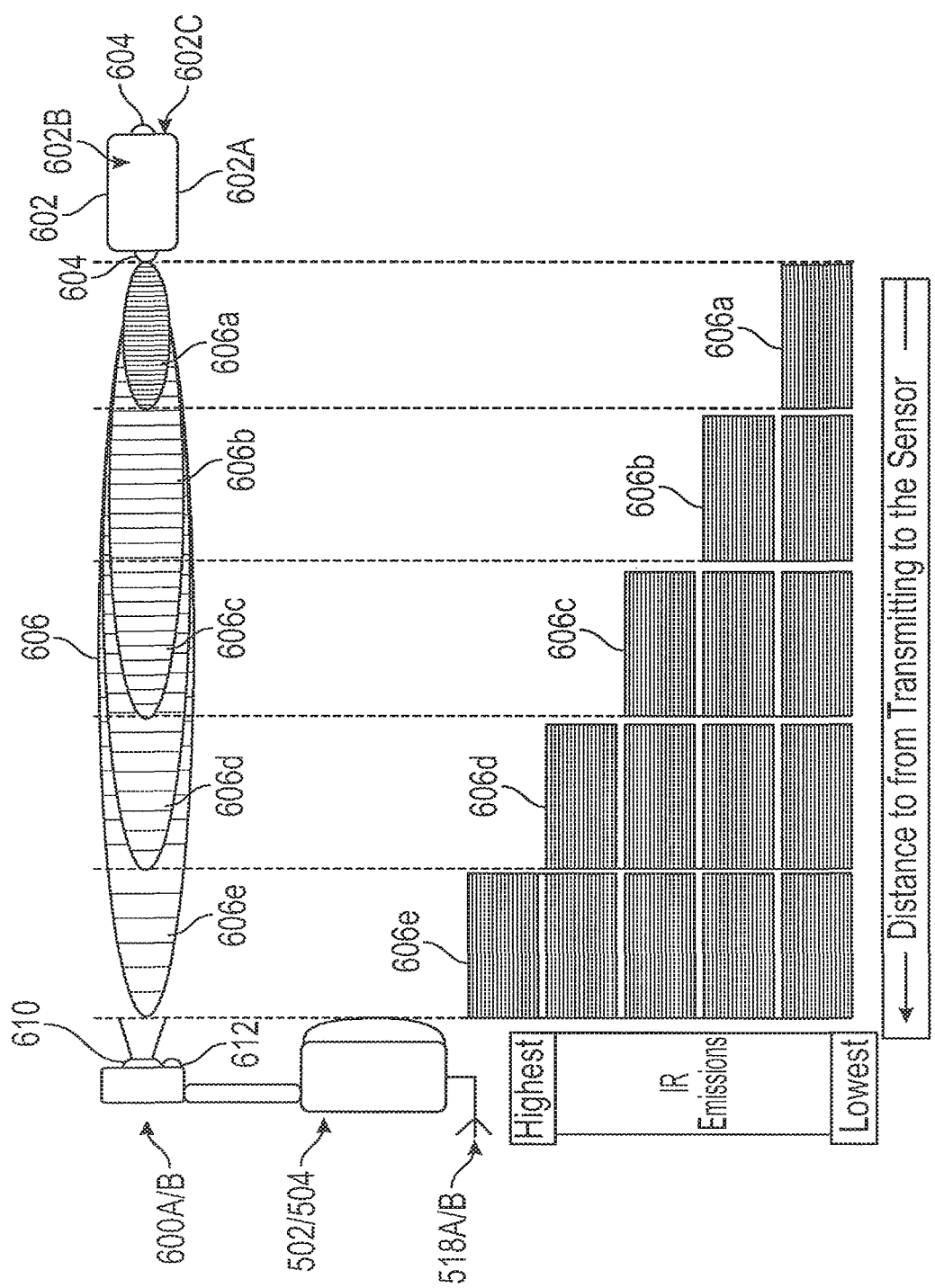

DISPENSING AND MONITORING SYSTEMS AND METHODS

CROSS REFERENCE TO RELATED APPLICATIONS

The present patent application is a continuation of U.S. patent application Ser. No. 16/732,013, filed Dec. 31, 2019, which claims the benefit of U.S. Provisional Patent Application No. 62/932,220, filed Nov. 7, 2019, and of U.S. Provisional Patent Application No. 62/787,622, filed Jan. 2, 2019.

INCORPORATION BY REFERENCE

U.S. patent application Ser. No. 16/732,013, filed Dec. 31, 2019, U.S. Provisional Patent Application No. 62/932,220, filed Nov. 7, 2019, and U.S. Provisional Patent Application No. 62/787,622, filed Jan. 2, 2019, are specifically incorporated by reference herein as if set forth in their entireties.

TECHNICAL FIELD

This disclosure generally relates to dispensers and, more particularly, to electronic dispensers for flexible sheet materials, such as paper products, or electronic dispensers for liquids, such as liquid soaps or hand sanitizers. Other aspects are also described.

BACKGROUND

Automated sheet material (e.g., paper towels, tissue, etc.) and fluid dispensers (e.g., liquid soap, hand sanitizer, etc.) are in wide use in a variety of public or commercial environments for sanitary and hygiene purposes and to help control the amounts of paper or fluids dispensed. In addition, to control the amounts of sheet material or fluids dispensed per operation/use of these dispensers, energy consumption and conservation of battery life for such automated sheet material and fluid dispensers is important, as over-use will lead to increased loss of battery power. A major drawback to some automated dispensers is the steady state current battery life consumption percentage, due to the dispenser being in a substantially active state and always looking for the next user. Such steady state current consumptions often can utilize upwards of 50 to 80% of a dispenser's battery capacity, depending on actual daily use. Such power drains/consumption can be more problematic in smaller dispenser units, for example, in dispensers used in residential and/or low traffic areas where smaller size batteries, i.e., "C" or "D" cell batteries, generally are used due to size, by requiring closer monitoring and more frequent change-out of spent batteries. Such automated dispensers further can be used as part of tracking or monitoring systems for tracking or mapping movements within certain facilities, which can sometimes require additional circuitry or components that can increase the power demands of such dispensers.

Accordingly, it can be seen that a need exists for systems and methods for dispensers that helps to drastically reduce steady state current consumption, while allowing the dispenser to respond to any user at any time. The present disclosure addresses these and other related and other related issues in the art.

SUMMARY

Briefly described, the present disclosure includes a dispensing and monitoring system for a facility. The dispensing and monitoring system can include a plurality of dispensers. Each dispenser of the plurality of comprising at least one passive infrared radiation sensor and a control system. The at least one passive infrared radiation senor is configured to capture infrared radiation of one or more individuals within a prescribed detection range, area, or zone covered by the at least one passive infrared radiation sensor. The control system is in communication with a power source and the at least one passive infrared radiation sensor. The control system further is configured to disconnect or decouple from the power source when the at least one passive infrared radiation sensor does not capture infrared radiation of one or more individuals within the prescribed detection range, area, or zone, and to connect or couple to the power source when the at least one passive infrared radiation sensor captures infrared radiation of one or more individuals within the prescribed detection range, area, or zone. In addition, each of the plurality of dispensers is positioned at selected locations about the facility, and each control system thereof is configured to capture information related to movements and/or activities of individuals within the facility to facilitate identifying, logging, mapping, and/or tracking of the movements and/or activities of the individuals throughout the facility.

The dispensing and monitoring system also can include a plurality of badges carried by the individuals throughout the facility. Each badge of the plurality of badges is configured to communicate with the plurality of dispensers to provide information identifying, mapping, and/or tracking of movements of the individuals throughout the facility.

Each badge of the plurality of badges can include a transmitter configured to transmit a plurality of signals, which each include signature information identifying a corresponding badge from which each signal is sent and an identifying code for identifying each signal.

Each signal of the plurality of signals further can be transmitted at a predetermined distance or at a predetermined signal strength, and the control system of one or more dispensers of the plurality of dispensers can be configured to determine a plurality of positions or movements of each badge in relation to the plurality of dispensers, based on the distance or signal strength of different signal of the plurality of signals received from each badge at the plurality of receivers.

The facility can include a medical facility. The medical facility can include at least one database configured to store information related to patients and the individuals moving throughout the medical facility. The dispensing and monitoring system further can be configured to cross-reference the information stored in the database with information identifying, mapping and/or tracking the movements of the individuals within the facility.

One or more dispensers of the plurality of dispensers can include a long range transmitter/receiver that facilitates communication between the one or more dispensers and a network. The one or more dispensers can transmit captured information related to movements and/or activities of the individuals to the network with the long range transmitter.

In embodiments, one or more of the plurality of dispensers can include a sheet material dispenser, and/or one or more of the plurality of dispensers can include a liquid dispenser.

In addition, according to the present disclosure, the plurality of dispensers can include at least one lead dispenser, and one or more drone dispensers in communication with the at least one lead dispenser. The one or more drone dispensers can communicate information captured thereby to the at least one lead dispenser.

For example, the one or more drone dispensers transmit one or more alerts or notifications to the at least one lead dispenser if the one or more drone dispensers are experiencing an error condition, a low power condition, or a low supply condition.

A power source of the at least one lead dispenser can remain connected to a control system of the at least one lead dispenser when a passive infrared radiation sensor of the lead dispenser or any of the one or more drone dispensers captures infrared radiation of one or more individuals within a prescribed detection range, area, or zone covered thereby.

Further, the power source of the at least one lead dispenser can be disconnected from the control system of the at least one lead dispenser when infrared radiation of one or more individuals is not detected within the prescribed detection range, area, or zone covered thereby and the passive infrared radiation sensors of the lead dispenser or one or more drone dispensers for a selected time period.

In another aspect, the present disclosure is directed to a method of monitoring movement of individuals in a facility. The method includes capturing infrared radiation emitted by one or more of individuals moving within a prescribed detection range, area, or zone covered using at least one passive infrared radiation sensor of at least one dispenser of a plurality of dispensers located about the facility. The method includes identifying, logging, mapping, and/or tracking of the movements and/or activities of each individual in relation to each dispenser that detects the individual. The method includes connecting the control system of the dispenser with a power source when the at least one passive infrared radiation sensor captures infrared radiation of one or more individuals within the prescribed detection range, area, or zone. Additionally, the method includes disconnecting control system of the dispenser of the plurality of dispenser from the power source of the dispenser when the at least one passive infrared radiation sensor does not capture infrared radiation of one or more individuals within the prescribed detection range, area, or zone.

The method also can include transmitting one or more signals from a plurality of badges carried by the individuals throughout the facility; and receiving the one or more signals at one or more of the plurality of dispensers to facilitate the identifying, mapping, and/or tracking of movements and/or activities of the individuals throughout the facility.

The method also can include cross-referencing information related to the individuals stored in a database with information related to identified, mapped, and/or tracked movements and/or activities of the individuals.

Further, the method can include transmitting information from a set of drone dispenser of the plurality of dispensers to a lead dispenser of the plurality of dispensers.

Still further, the method can include connecting a power source of the lead dispenser when a passive infrared radiation sensor of any of the set of drone dispensers captures infrared radiation of one or more individuals within a prescribed detection range, area, or zone covered thereby.

In one aspect, the present disclosure is directed to a dispenser with a power management system. The dispenser comprises a supply of liquid or sheet material, and a dispenser housing in which the supply is received. The dispenser comprises a dispensing mechanism located within the dispenser housing in communication with the supply and configured to dispense prescribed amounts of the supply from the dispenser housing. The dispenser comprises a proximity sensor positioned along the dispenser housing and configured to detect a presence of a user proximate the dispenser. The dispenser also comprises a controller in communication with the dispensing mechanism and the proximity sensor. The controller is configured to activate the dispensing mechanism to dispense the prescribed amounts of the supply upon receipt of one or more signals from the proximity sensor indicative of the presence of the user proximate the dispenser. And, the dispenser comprises a power source supplying power to the controller, dispensing mechanism and proximity sensor.

The dispenser also comprises a power management system in communication with the controller and comprising a passive infrared radiation sensor arranged along the dispenser housing and configured to detect infrared radiation emitted by one or more users within a prescribed detection range, area, or zone of the dispenser. When the passive infrared radiation sensor does not capture infrared radiation within the prescribed detection range, area, or zone, the dispenser is placed in a low power state with the passive infrared sensor remaining connected to the power source and the controller, the dispensing mechanism, and/or the proximity sensor being disconnected from the power source. When the at least one passive infrared radiation sensor captures infrared radiation within the prescribed detection range, area, or zone, the controller, the dispensing mechanism, and/or the proximity sensor are connected with the power source.

The dispenser further can comprise a switch coupled to the power source and the controller, proximity sensor, and/or the dispensing mechanism. The switch is responsive to one or more signals from the passive infrared radiation sensor to decouple the power source from the controller, proximity sensor, and/or the dispensing mechanism, such that the controller, proximity sensor, and/or the dispensing mechanism do not consume power from the power source. In one embodiment, the switch can comprise a triode.

In some embodiments, when the passive infrared radiation sensor does not capture infrared radiation within the prescribed detection range, area, or zone, the passive infrared radiation sensor outputs one or more low level signals to the controller. Upon receipt of the one or more low level signals from the passive infrared radiation sensor at the controller, the controller initiates a shutdown sequence to complete any ongoing work, functions, or operations of the controller. Upon completion of the shutdown sequence, the controller outputs one or more signals to the switch such that the switch decouples the power source and the controller, proximity sensor, and/or the dispensing mechanism.

In one embodiment, the dispenser consumes less than about 100 $\mu$A in the low power state. In another embodiment, the dispenser consumes less than about 50 $\mu$A in the low power state. In yet another embodiment, the dispenser consumes less than about 30 $\mu$A to less than about 20 $\mu$A in the low power state.

The dispenser further can include a passive infrared radiation sensor controller that is integrated with the passive infrared radiation sensor. The passive radiation sensor controller is configured to generate one or more signals responsive to signals received from the passive infrared radiation sensor to connect and disconnect the controller, dispensing mechanism, and proximity sensor to and from the power source.

The dispenser further can comprise a timer that is integrated with the passive infrared radiation sensor. The timer can be activated when the passive infrared radiation sensor does not detect infrared radiation within the prescribed detection range, area, or zone. Upon expiration of the timer, the power source can be disconnected from the controller, proximity sensor, and/or the dispensing mechanism.

In one embodiment, the dispenser includes a sheet material dispenser, and the dispensing mechanism includes a feed roller that is configured engage and move sheet material from the supply of sheet along a discharge path and out of the dispenser for dispensing thereof.

In another embodiment, the dispenser includes a liquid dispenser; the supply of liquid includes a supply chamber that stores a liquid; and the dispensing mechanism includes a pump that directs the liquid from the supply chamber to the discharge.

In one aspect, the present disclosure is directed to a dispensing system comprising a lead dispenser and a plurality of drone dispensers.

The lead dispenser includes a control circuit for controlling one or more operations of the lead dispenser, and at least one passive infrared radiation sensor in communication with the control circuit. The passive infrared radiation sensor is configured to capture infrared radiation indicative of one or more individuals present within a prescribed detection range, area, or zone of the lead dispenser.

The plurality of drone dispensers each are configured to communicate information to the lead dispenser. Each of the plurality of drone dispensers include a control circuit for controlling one or more operations of each done dispenser and a passive infrared radiation sensor in communication with the control circuit of each drone dispenser. The passive infrared radiation sensor of each drone dispenser is configured to capture infrared radiation indicative of one or more individuals present within a prescribed detection range, area, or zone of each drone dispenser. When the passive infrared radiation sensor of one of the drone dispensers does not capture infrared radiation, the control circuit of that drone dispenser is disconnected from a power source thereof.

The dispensing system also comprises a network in communication with the lead dispenser. The lead dispenser is configured to communicate information related to the lead dispenser and the information received from the plurality of drone dispensers to the network.

With the dispensing system, a power source of the lead dispenser remains connected to the control circuit of the lead dispenser when passive infrared radiation sensors of the lead dispenser or of any of the plurality of drone dispensers capture infrared radiation indicative of one or more individuals present within the prescribed range, area or zone thereof.

In embodiments, one or more of the plurality of drone dispensers includes a sheet material dispenser, and/or one or more of the plurality of drone dispensers includes a liquid dispenser.

The plurality of drone dispensers can transmit one or more alerts or notifications to the lead dispenser if the one or more drone dispensers are experiencing an error condition, a low power condition, and/or a low supply condition, and the lead dispenser can transmit the one or more alerts or notifications from the plurality of drone dispensers to the network.

The lead dispenser can include a long range transmitter/receiver that facilitates communication between the lead dispenser and the network.

These and other advantages and aspects of the embodiments of the disclosure will become apparent and more readily appreciated from the following detailed description of the embodiments and the claims, taken in conjunction with the accompanying drawings. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the embodiments of the present disclosure, are incorporated in and constitute a part of this specification, illustrate embodiments of the invention, and together with the detailed description, serve to explain the principles of the embodiments discussed herein. No attempt is made to show structural details of this disclosure in more detail than may be necessary for a fundamental understanding of the exemplary embodiments discussed herein and the various ways in which they may be practiced.

FIGS. 1A-C shows a perspective, partial cutaway views of an example sheet material dispenser according to principles of the present disclosure.

FIG. 10B illustrates an overview example of a badge transmitting a series of signals and primary receivers configured to receive these signals according to another aspect of the present disclosure.

DETAILED DESCRIPTION

The following description is provided as an enabling teaching of embodiments of this disclosure. Those skilled in the relevant art will recognize that many changes can be made to the embodiments described, while still obtaining the beneficial results. It will also be apparent that some of the desired benefits of the embodiments described can be obtained by selecting some of the features of the embodiments without utilizing other features. Accordingly, those who work in the art will recognize that many modifications and adaptations to the embodiments described are possible and may even be desirable in certain circumstances. Thus, the following description is provided as illustrative of the principles of the embodiments of the present disclosure and not in limitation thereof.

Figure 1C:
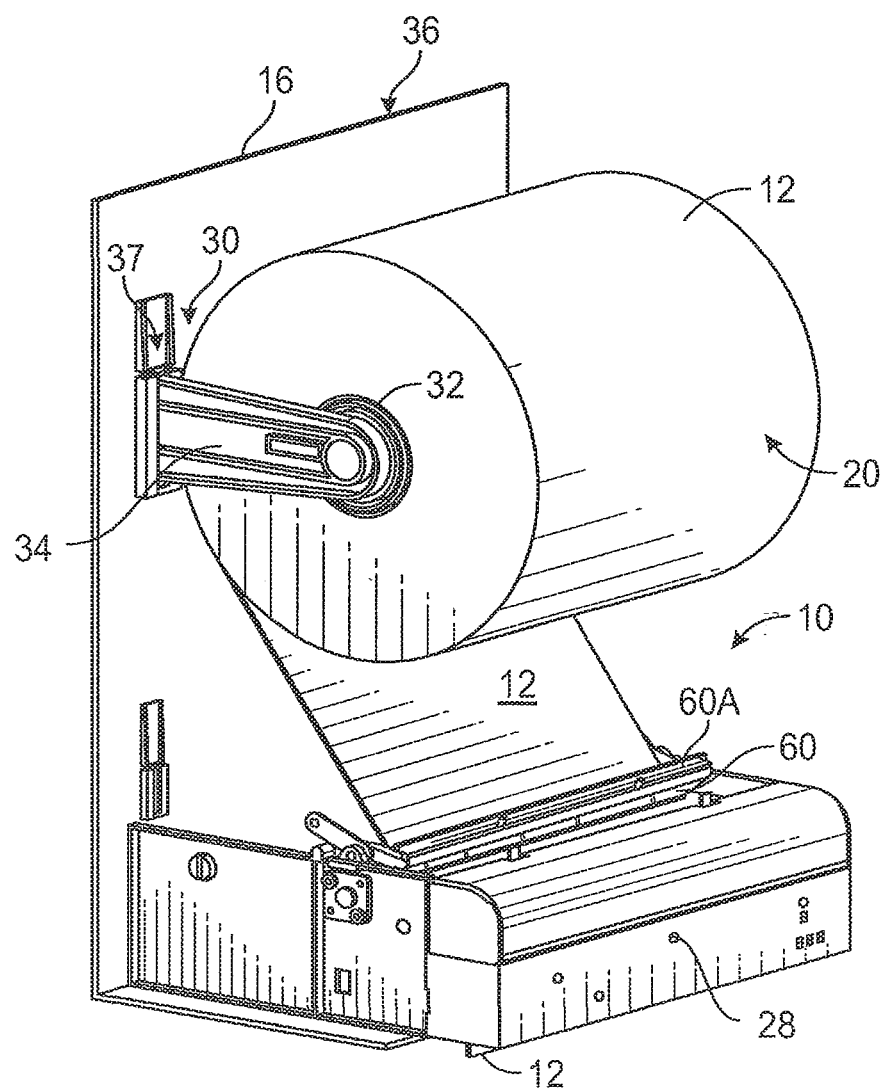

As generally illustrated in FIGS. 1A-1C and 3, the present disclosure is directed to dispensers that can be automated dispensers 10 for feeding or dispensing a flexible sheet material 12, or dispensers 300 for dispensing fluid materials. In one aspect, as shown in FIGS. 1A-1C, the dispenser 10 can dispense various types of sheet materials including paper sheet materials, such as towels, tissue, napkins, etc. The dispenser 10 generally will include a dispensing mechanism including driven feed roll drive assembly/system 14 mounted or otherwise disposed within a dispenser housing 16 and operable to dispense prescribed amounts/lengths of sheet material. For example, upon activating the dispenser 10, the feed roller drive assembly 14 is engaged and operates to drive or cause rotation of a feed roller or drive spindle 18. The rotation of the feed roller 18 in turn pulls the sheet material 12 from a supply of sheet material 20 for feeding a predetermined, prescribed, measured or selected amount or length L (e.g., a 10"-12" or other desired length) of sheet material 12 along a conveying or feed path P (FIG. 1B) from the roll or supply 20 of the sheet material 12 through and out of a discharge, such as a discharge chute 22 or other suitable opening provided/defined in the housing 16 of the dispenser 10, as is generally indicated in FIG. 1B.

Figure 4:
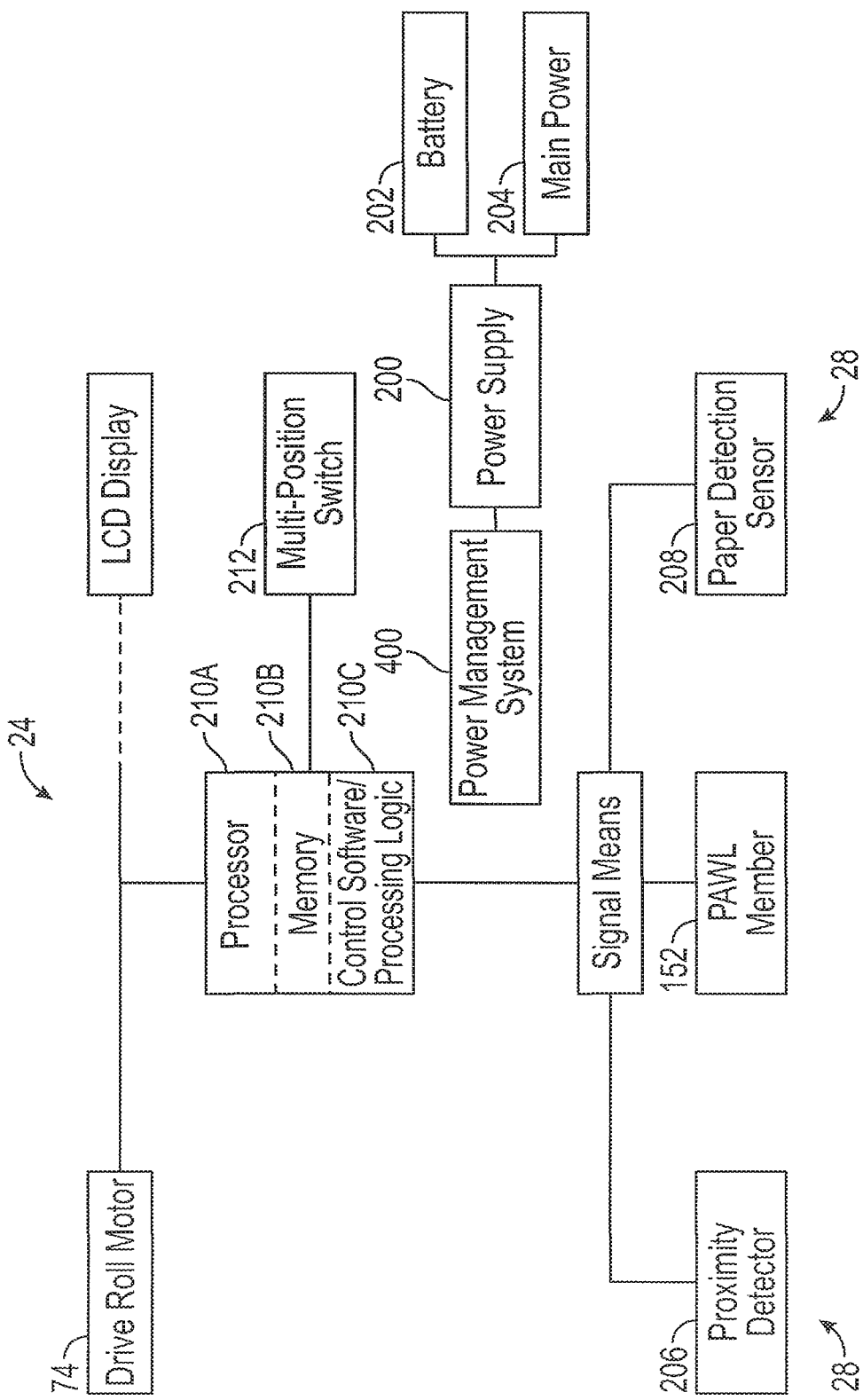
FIG. 4 shows a block diagram of an example of a control system in communication with the dispenser assembly according to one aspect of the present disclosure.

The feed roller drive assembly 14 can be activated and driven/rotated to pull and feed the sheet material 12 from the sheet material supply 20 to and through the discharge chute 22 upon receiving a signal from a control system or control circuit 24 of the dispenser 10. An example of a control system 24 for a dispenser is generally shown in FIG. 4. The control system 24 can include a controller or control unit 210 including a processor 210A, such as a microprocessor, CPU, etc., a memory 210B, and computer programming 210C stored in the memory 210B and executed by the processor 210A for control of the feed roller drive assembly 14 to feed the selected or desired length of sheet material and to monitor the dispenser 10 and components such as the supply of sheet material and usage/operation of the dispenser. The controller 210 further will be in communication with, and will receive a plurality of signals, from a sensor or an array or series of sensors, such as generally indicated at 28, to control dispensing of the sheet material 12.

The sensors 28 can include various type sensors or detectors, for example, including an adjustable proximity sensor that can be configured/adjusted to detect the presence of a user's hand or other object at a desired range/location and dispense measured/selected amounts of sheet material 12. The proximity sensor can be manually or automatically adjustable. In addition, or in the alternative, one or more pairs of IR sensors (e.g., an emitter and a corresponding detector) that are arranged about/within the discharge chute 22 and transmit/receive signals across the discharge path P to sense or detect the presence or absence of sheet material or other object within the discharge chute or otherwise along the feed path. Any suitable sensor, however, such as a photoelectric, light curtain, or other similar sensing systems/detectors, can be used to detect the presence of a user's hands or other object placed along the dispenser housing 16, and/or the feeding of a selected amount of sheet material 12 can be used, without departing from the present disclosure. In addition, various sensor arrays and/or control systems can be used, such as disclosed in U.S. patent application Ser. Nos. 15/185,937, and 14/256,019, the complete disclosures of which are incorporated by reference as if set forth fully herein.

It further should be appreciated that the sheet material dispenser 10 described herein should not be considered to be limited to any particular style, configuration, or intended use, or to a particular type of sheet material. For example, the dispenser 10 may be operable to dispense paper towels, toilet tissue, or other similar paper or sheet materials, including dispensing or feeding non-perforated and/or perforated sheet materials.

As indicated in FIGS. 1A and 1C, the dispenser housing 16 includes a roll support mechanism 30, for holding at least one roll 32 of the supply 20 of sheet material 12. The roll support mechanism 30 can include a pair of supports or arms 34 coupled to the dispenser housing 16 and supporting the roll 32, such as indicated at 36. These arms/supports 34 may be fixedly arranged to hold the supply 20 of sheet material in a spaced relationship with respect to the feed roller 18. For example, the support arms 34 can be attached or coupled to the dispenser housing 16 by sliding or snap-fitting at least a portion of the supports/arms within grooves or slots 37 defined along a rear portion 36 of the dispenser housing 16. However, the support arms 34 can be connected to the dispenser housing 16 in any suitable manner, such as with one or more fasteners or other suitable connection mechanisms. As a further alternative, the support arms also can be integrally formed with the housing without departing from the present disclosure. In additional or alternative constructions, the support arms 34 also may be biased or urged, such as by a spring or other suitable biasing mechanism(s), or by a general resiliency, toward the feed roller 18 to urge or direct the supply 20 of sheet material downwardly toward or against the feed roller 18.

The feed roller 18 is movably or rotatably coupled to one or more walls or other portions of the dispenser housing 16. For example, the ends of the feed roller 18 can be connected, mounted, or otherwise coupled to the dispenser housing 16 by one or more bearing assemblies and/or other suitable support mechanisms that support and allow for rotation of the feed roller 18 in relation to the dispenser housing 16.

As illustrated in FIGS. 1B, the dispenser assembly 10 further generally can include one or more pressing rollers 60. The pressing rollers 60 can be biased toward engagement with the feed roller 18, so as to engage and urge or press the sheet material 12 against the feed roller 18 with a force sufficient to draw or pull the sheet material 12 therebetween upon rotation of the feed roller 18. The pressing roller(s) 60 can be mounted within the dispenser housing 16, such as with the ends thereof held within one or more arms or supports of a bracket 60A in a manner to enable rotation of the pressing roller(s) 60. The bracket 60A also can be biased by a biasing member, such as a spring, so that the pressing rollers 60 can be urged toward the driven feed roller 18. Additionally, or in the alternative, one or more pressing roller(s) 60 further can be disposed within a frame or other structure and biased toward the feed roller 18 such as by compressing/tension springs or other suitable springs, biased cylinders or other biasing mechanisms. In one construction, the frame can support at least two pressing rollers and also can be pivotable to enable one pressing roller to move away from the feed roller as needed, while the other roller is pivoted into closer contact with the feed roller (not shown). In addition, or alternatively, the pressing rollers 60 may be driven by drive mechanism, for example, off of the motor that drives the feed roller or by a separate drive, so as to facilitate feeding of the sheet material 12.

The feed roller drive assembly 14 includes at least one driving mechanism, e.g., a motor 74, that is in communication with the feed roller 18 so as to drive movement/rotation thereof (FIG. 1C). The motor 74 can include a brushless servo or stepper motor or other, similar type of variable speed electric motor, and communicates with the control system 24 of the dispenser 10 to receive instructions and power for activating and driving the feed roller 18 through a dispensing cycle (e.g., a determined time, number of revolutions, etc.), so as to feed the selected or desired amount/length of the sheet material through the discharge chute 22 of the dispenser 10. In one additional aspect, the drive system/assembly 14 also can include a transmission assembly 76 for transferring power between the motor 74 and the feed roller 18. For example, the transmission assembly 76 can include a drive belt 78 and/or drive gears coupling the motor 74 to the feed roller 18. In alternative constructions, the feed roller drive assembly 14 can include a gear assembly including a plurality of intermeshing gears that operatively connect the driving mechanism 74 and the feed roller 18. Any suitable transmission mechanisms, device, assemblies, etc. can be used for transferring power between the driving mechanism and the feed roller, without departing from the scope of the present disclosure.

The sheet material dispenser 10 also can include a cutting mechanism/assembly 150 for cutting or severance of dispensed sheet material. In one embodiment, as shown in FIGS. 2A and 2B, the dispenser housing may include one or more tear bars or other suitable cutting members 151 disposed adjacent or along the dispenser housing 16 so that a user can separate a sheet or measured amount of the material by grasping and pulling the sheet across the tear bar 151.

Figure 2A:
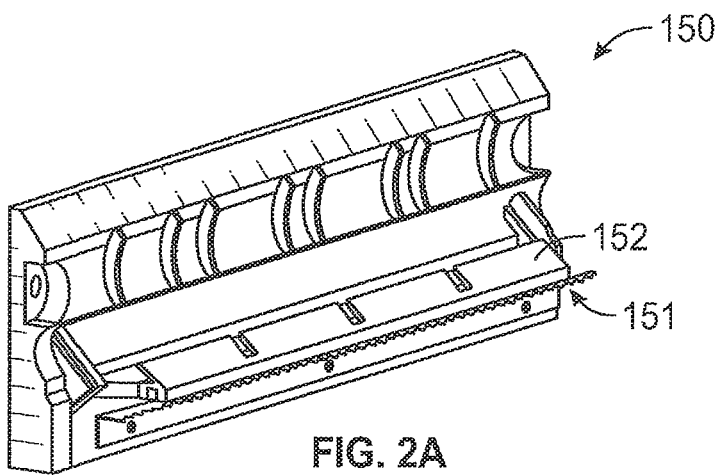
FIGS. 2A-2B provide examples of a tear bar and pivotable pawl member that can be provided for assisting in control of the dispenser according to aspects of the present disclosure.
Figure 2B:
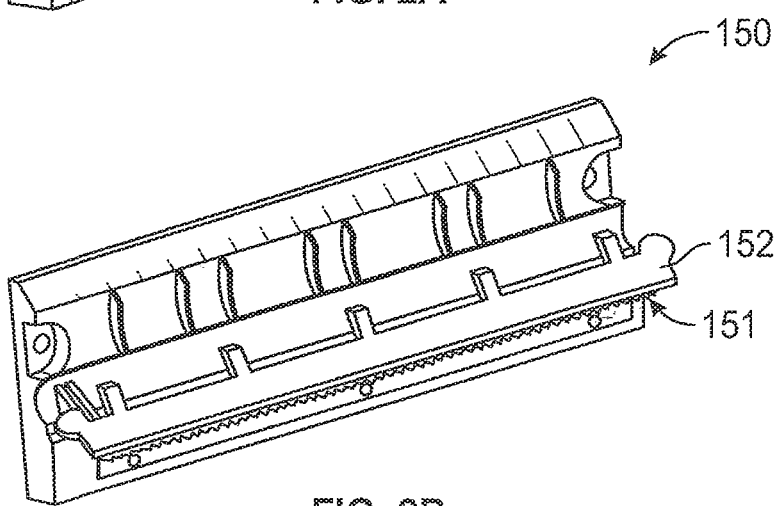

In addition, as also shown in FIGS. 2A and 2B, a pivotally mounted pawl member 152 can be located proximate to the stationary tear bar 151 such that movement of sheet material 12 into the tear bar 151 for severance pivots the pawl member 152 between multiple positions. A signal device such as a proximity sensor switch or the like, cooperative with the pawl member 152, can also be arranged such that movement of the pawl member 152 between various positions causes the signal means to send a signal to notify the controller 210 that the sheet material has been removed. By way of example, such signal means can include an infrared emitter and detector that detects movement of the pawl member 152 between first and second positions, though any suitable sensor can be employed such as a proximity sensor or other detector, a magnetic switch, or a mechanical switch. After receiving a signal indicating removal of the sheet material, the control system 24 further can activate a paper detection sensor 158 (FIG. 4) to verify that the sheet material has been removed from the discharge chute. An example of such a mechanism is shown in U.S. patent application Ser. No. 13/155,528, the disclosure and figures of which is incorporated herein by reference herein as if set forth in their entirety.

In alternative constructions, the cutting mechanism can be configured to move or be actuated at a prescribed or preset point during a revolution of the feed roller 18, or after a prescribed rotation of the feed roller 18 so as to selectively cut or perforate the sheet material after a desired or prescribed length or portion of the sheet material has been fed or dispensed. For example, embodiments of the present disclosure described herein can utilize concepts disclosed in commonly-owned U.S. patent application Ser. Nos. 15/185, 937 and 15/848,643, the disclosure and figures of which are incorporated by reference herein as if set forth in their entireties.

Figure 3:
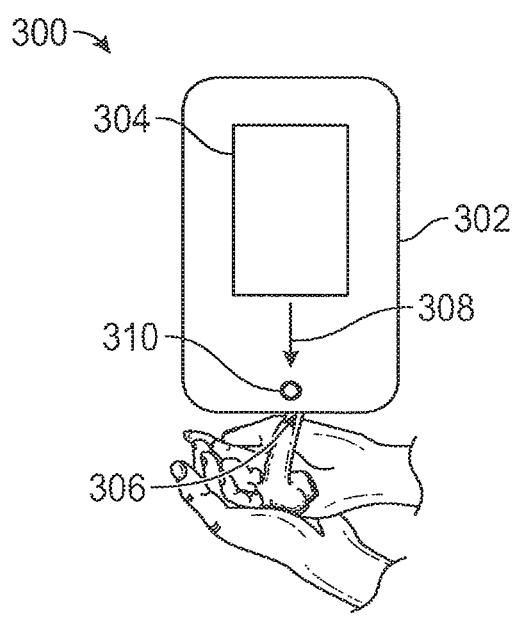
FIG. 3 shows a schematic diagram of a fluid dispenser according to one aspect of the present disclosure.

FIG. 3 shows a schematic diagram of a liquid or fluid dispenser 300 according to one embodiment of the present disclosure. The liquid dispenser 300 generally includes a dispenser housing 302 that supports/houses a supply chamber or reservoir 304 that contains/stores a liquid, e.g., liquid soap, hand sanitizer, etc. The liquid dispenser 300 further includes one or more nozzles or other suitable discharge outlet 306 for providing the liquid to the user, and the liquid dispenser includes a dispensing mechanism including a pumping system or mechanism 308, e.g., including one or more pumps or other suitable actuators, for directing or moving the liquid from the supply chamber 304 to the discharge outlet 306. The liquid dispenser 300 further includes one or more sensors 310, e.g., including an IR sensor, in communication with a controller, such as controller 510A/510B shown in FIGS. 8A-8B, that is configured to control operation of the pumping mechanism 308. The one or more sensors 310 can be configured as proximity sensors to gather information that is related to the presence of an object, such as a user's hand, near or proximate the dispenser 300. Accordingly, in operation, when a user places their hand in proximity to the one or more sensors 310, the one or more sensors 310 provide a signal to the controller to activate the pumping mechanism 308 for dispensing a select or prescribed amount of liquid. The controller further is coupled to a power source, e.g., one or more batteries or an AC power source, such as power source 514A/514B in FIG. 8A/8B to power the controller, dispensing mechanism 308, and the one or more sensors 310.

FIG. 4 illustrates a block diagram of an electronic control system or circuit 24 for operating the dispenser 10 in an exemplary embodiment. The dispenser assembly 10 or operative components thereof may be powered by a power supply 200, such as one or more batteries 202 contained in a battery compartment, though any suitable battery storage device may be used for this purpose. Alternatively, or in addition to battery power, the power supply 200 may also include a building's alternating current (AC) distribution system as indicated at 204. For this purpose, a plug-in modular transformer/adapter could be provided with the dispenser 10, which connects to a terminal or power jack port located, for example, in the bottom edge of the circuit housing for delivering power to the control system 24 and associated components. The control system 24 also may include a mechanical or electrical switch that can isolate the battery circuit upon connecting the AC adapter in order to protect and preserve the batteries.

In one example embodiment, the control system 24 can include or otherwise communication with a sensor 28, such as a proximity sensor or other detector 206, configured to capture information related to detect an object placed in a detection zone external to the dispenser to initiate operation of the dispenser, e.g., to detect a presence of a user or a user's hand within a prescribed zone, area or range of the sensor 28. This sensor 28 may be a passive infrared sensor that detects changes in ambient conditions, such as ambient light, capacitance changes caused by an object in a detection zone, and so forth. In an alternate embodiment, the sensor 28 may be an active device and include an active transmitter and associated receiver, such as one or more infrared (IR) transmitters and an IR receiver. The transmitter transmits an active signal in a transmission cone corresponding to the detection zone, and the receiver detects a threshold amount of the active signal reflected from an object placed into the detection zone. The control system 24 generally will be configured to be responsive to the sensor 28 for initiating a dispense cycle upon a valid detection signal therefrom. For example, the proximity sensor 206 or other detector can be used to detect both the presence of a user's hand. The dispenser 10 can additionally include a paper detector sensor 208, such as one or more infrared emitters and infrared detectors with one infrared emitter/detector, pair aligned to detect a user's hand below the dispenser 10 and the second infrared emitter/detector pair aligned to detect a sheet hanging below the outermost front edge of the discharge.

The controller 210 of the control system 24 can to control activation of the dispensing mechanism 74, e.g., upon valid detection of a user's hand by the sensor 28 for dispensing a measured length of the sheet material 12. In one embodiment, the controller 210 can track the running time of the drive motor 74 of the motorized feed roller, and/or receive feedback information directly therefrom indicative of a number of revolutions of the feed roller 18 and correspondingly, an amount of the sheet material feed thereby. In addition, or as a further alternative, sensors and associated circuitry may be provided for this purpose. Various types of sensors can include IR, radio frequency (RF), capacitive or other suitable sensors, and any one or a combination of such sensing systems can be used. The controller 210 also can control the length of sheet material dispensed. Any number of optical or mechanical devices may be used in this regard, such as, for example, an optical encoder may be used to count the revolutions of the drive or feed roller 18, with this count being used by the controller 210 to meter the desired length of the sheet material to be dispensed.

The processing logic for operation of the electronic dispenser in, for example, the hand sensor and butler modes, can be part of the control software 210C stored in the memory 210B of the controller 210 or other memories included in the control system 24. One or more binary flags are also stored in memory and represent an operational state of the dispenser (e.g., "paper cut" set or cleared). An operational mode switch in dispenser sets the mode of operation. In the hand sensor mode, the proximity (hand) sensor detects the presence of a user's hand below the dispenser 10 and in response, the motor 74 is operated to dispense a measured amount of sheet material 12. The controller 210 can then monitor when the sheet of material is removed. For example, actuation of the pawl member 152 or triggering/activation of a paper detection sensor 208 can determine the removal of paper and reset the hand sensor. The proximity sensor 206 also can be controlled to not allow additional sheet material to be dispensed until the proximity sensor is reset. If the proximity sensor 206 detects the presence of a user's hand but does not dispense sheet material, the controller 210 can check for sheet material using the paper detection sensor 208. If sheet material 12 has not been dispensed (i.e., no sheet material is hanging from the dispenser), the motor 74 will be activated to dispense a next sheet.

A multi-position switch 212 also can be provided to switch the dispenser operation between a first or standard operation mode and a second mode, such as a butler mode. In such butler mode, the proximity sensor 208 for detecting the presence of a user's hand/object can be deactivated, and the control system 24 can automatically dispense sheet material when the cover is closed and the dispenser is put into operation. The paper detection sensor 208 further can determine if a sheet is hanging from the dispenser. If sheet material is hanging, the control system 24 will then monitor when the sheet of material is removed. For example, a cutting mechanism movement detector, which may be arranged and configured to detect actuation or movement of the cutting mechanism; the pawl member; and/or the paper detection sensor can determine the removal of paper and reset the dispenser. The next sheet will be dispensed automatically. If the paper detection sensor 158 determines the absence of hanging sheet material, the motor 74 will be activated to dispense the next sheet. The control system 24 can then determine if the sheet has been removed before dispensing another sheet.

In one embodiment, the dispenser assembly 10 is operative in a first mode to be responsive to a signal from the proximity sensor to dispense a sheet of material. The dispensing mechanism is operative in a second mode to dispense a next sheet in response to the signal means being activated by movement of the cutting mechanism or tear bar to its extended position in response to dispensed sheet material 12 being removed from the dispenser. In another embodiment, the dispenser 10 can be operative in a second mode to dispense a next sheet in response to a signal means being activated by movement of the cutting mechanism, and a signal from a paper detection sensor 208 that the sheet material 10 has been removed from the dispenser. Such a sensor can be affixed to an external surface of the discharge rather than inside the discharge.

The dispenser 10 generally can dispense a measured length of the sheet material, which may be accomplished by various means, such as a timing circuit that actuates and stops the operation of the motor driving the feed roller after a predetermined time. In one embodiment, the drive motor 74 can provide direct feedback as to the number of revolutions of the feed roller 18, indicative of an amount of the sheet material 12 fed thereby. Alternatively, a motor revolution counter can be provided that measures the degree of rotation of the feed roller 18 and is interfaced with the controller 210 or other control circuitry to stop a drive roller motor after a defined number of revolutions of the feed roller 18. This counter may be an optical encoder type of device, or a mechanical device. The control system 24 may include a device to allow maintenance personnel to adjust the sheet length by increasing or decreasing the revolution counter set point. The multi-position switch 212 can also be in operable communication with the controller 210 to select one of a plurality of time periods as a delay between delivery of a first sheet and delivery of a next sheet to the user. Embodiments of the present disclosure described herein can also utilize concepts disclosed in commonly-owned U.S. Pat. No. 7,213,782 entitled "Intelligent Dispensing System" and U.S. Pat. No. 7,370,824 entitled "Intelligent Electronic Paper Dispenser," both of which are incorporated by reference in their entireties herein.

Figure 5:
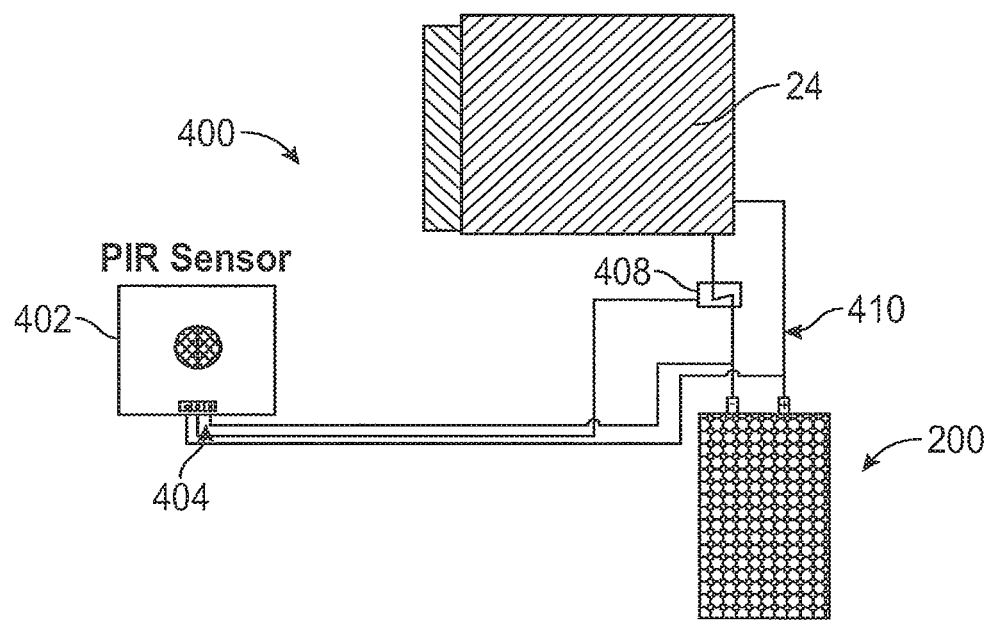
FIG. 5 shows a schematic view of a power management assembly according to one aspect of the present disclosure.
Figure 6:
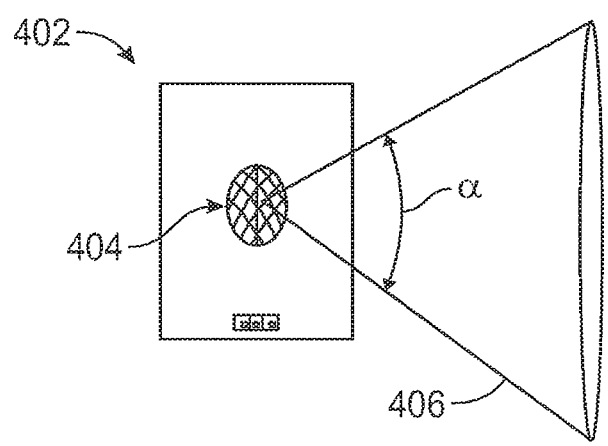
FIG. 6 shows a schematic view of an infrared radiation sensor of a power management assembly such as shown in FIG. 5.

As shown in FIGS. 5 and 6, the sheet material dispenser 10 or the fluid dispenser 300 also includes a power management assembly 400 that is configured to activate and deactivate the dispenser 10/300 based on a detected presence of a user within a prescribed area or zone around the dispenser 10/300. For example, the power management assembly 400 can include one or more sensors 402 that are configured to gather environmental information within the prescribed zone/area around the dispenser 10/300 to detect the presence of people/users as they enter and exit the area or zone where the dispenser is located, e.g., a restroom, hospital room, etc. For example, as further shown in FIGS. 4 and 5, the power management assembly 400 further can be integrated with or otherwise in communication with the dispenser's control system 24 to activate and deactivate the control system 24 based on the detected presence of people/users by the sensor(s) 402.

FIG. 6 shows that the one or more sensors 402 can include one or more passive infrared radiation ("PIR") sensor(s) 404 that are configured to detect infrared radiation of people/users, which is indicative of the presence or movement of the people/users within a prescribed detection range, area, zone, etc. 406 covered by the infrared radiation sensor 404. In one embodiment, as shown in FIG. 6, the detection area 406 of the one or more infrared radiation sensors 404 is generally conical with a detection range or angle α of about 110 degrees, though other suitable detection ranges/angles are possible, such as about 80 degrees, about 90 degrees, about 100 degrees, about 120 degrees, or more, without departing from the scope of the present disclosure.

Turning again to FIG. 5, the power management assembly 400 also can include a switch or switch circuitry 408, e.g., including a triode, or other suitable switching mechanism, that is coupled to a lead or other coupling/connector 410 connecting the power source 200 and the control system 24 of the dispenser. The switch 408 can be activated to connect and disconnect the control system 24 from the power source 200 (e.g., the switch 408 includes first, disconnected position where the control system 24 and the power source 200 are disconnected and the switch 408 includes a second, connected position wherein the control system 24 and the power source 200 are connected). In this regard, the switch 408 can couple the control system 24 to the power source 200 such that the control system 24 can draw or consume power from the power source 200, and the switch 408 can disconnect or decouple the control system 24 from the power source 200 (e.g., after a safe shutdown sequence of the controller 210) such that the control system 24 does not draw or consume power from the power source 200.

FIG. 5 further shows that the switch 408 can be connected to the infrared radiation sensor 404, such that the switch 408 can be activated to connect and disconnect the control system 24 and the power source 200 based on detection of or failure to detect a user/person. That is, the switch 408 is configured to couple and decouple the power source 200 and the control system 24 responsive to or based on signals received from the infrared radiation sensor 404. Thus, the switch 408 can decouple the power source 200 and the control system 24 when the PIR sensor 404 does not capture radiation of one or more persons or individuals (so that no power is consumed from the power source 200 by the control system 24 during such a non-operative state), and can re-engage or couple the power source 200 and the control system 24, so that the control system 24 can receive/draw power from the power source when the PIR sensor 404 captures radiation of one or more persons or individuals. The PIR sensor 404 remains connected to the power source 200 and consumes a minimal amount of power therefrom (FIG. 5).

In operation, the power management assembly 400 initially is in a low power mode or state, in which the control system 24 of the dispenser is deactivated (e.g., the switch 408 is in the first, disconnected or decoupled position in which the control system 24 is not connected to, i.e., not in communication with the power source 200). When a user/person enters the area or zone 406 covered by the PIR sensor 404, in response to a detection thereof, the power management assembly 500 can be switched to an active mode and activates the dispenser/the control system 24 to allow normal function thereof, such as by engaging the switch 408 to change from a first, disconnected state to its second, connected/coupled or operative state in which the control system 24 is connected to the power source 200). When no users are within the area or zone covered by the one or more PIR sensors 404, the power management assembly 400 returns dispenser back to a low or minimal power mode (e.g., once the detected users/people have left the area/zone covered by the infrared radiation sensor(s) 404, and/or after the selected period of no detected activity/presence, the switch 408 is returned its first, disconnected state again disconnecting the control system 24 from the power source 200).

In the low power mode or state, with the control system 24 disconnected, generally only the PIR sensor 404 will draw power from the power source 200. The PIR sensor 404 uses about one-tenth of power demands that the control system 24, e.g., the current use of the infrared radiation sensor can be about 50 μA (and in some embodiments as low as about 30 μA to about while the current of the control system 24 is about 500 μA. Accordingly, in some embodiments, the dispenser 10/300 can consume less than about 50 μA in the low power state; in other embodiments, the dispenser can consume less than about 30 μA in the low power state; and in further embodiments, the dispenser can consume less than about 15 μA in the low power state; and in even further embodiments, the dispenser can consume less than about 10 μA in the low power state.

In alternative embodiments, one or more components of the dispenser, e.g., proximity sensors, monitoring systems, dispensing mechanisms, etc. may still be connected to the power source and draw at least some power therefrom in the low power state, and thus, in those alternative embodiments, the dispenser can consume less than about 250 μA, less than about 200 μA, less than about 150 μA, or less than about 100 μA in the low power state.

According to the present disclosure, the term about can be understood to cover values in the range of ±0.5 μA, though about can reflect any suitable value range, such as ±0.1 μA, ±1 μA, or up to ±3 μA, or other value ranges as will be understood by those skilled in the art. In this regard, the power management system according to embodiments of the present disclosure helps to save significant power in comparison to typical steady state dispensing systems.

Figure 7:
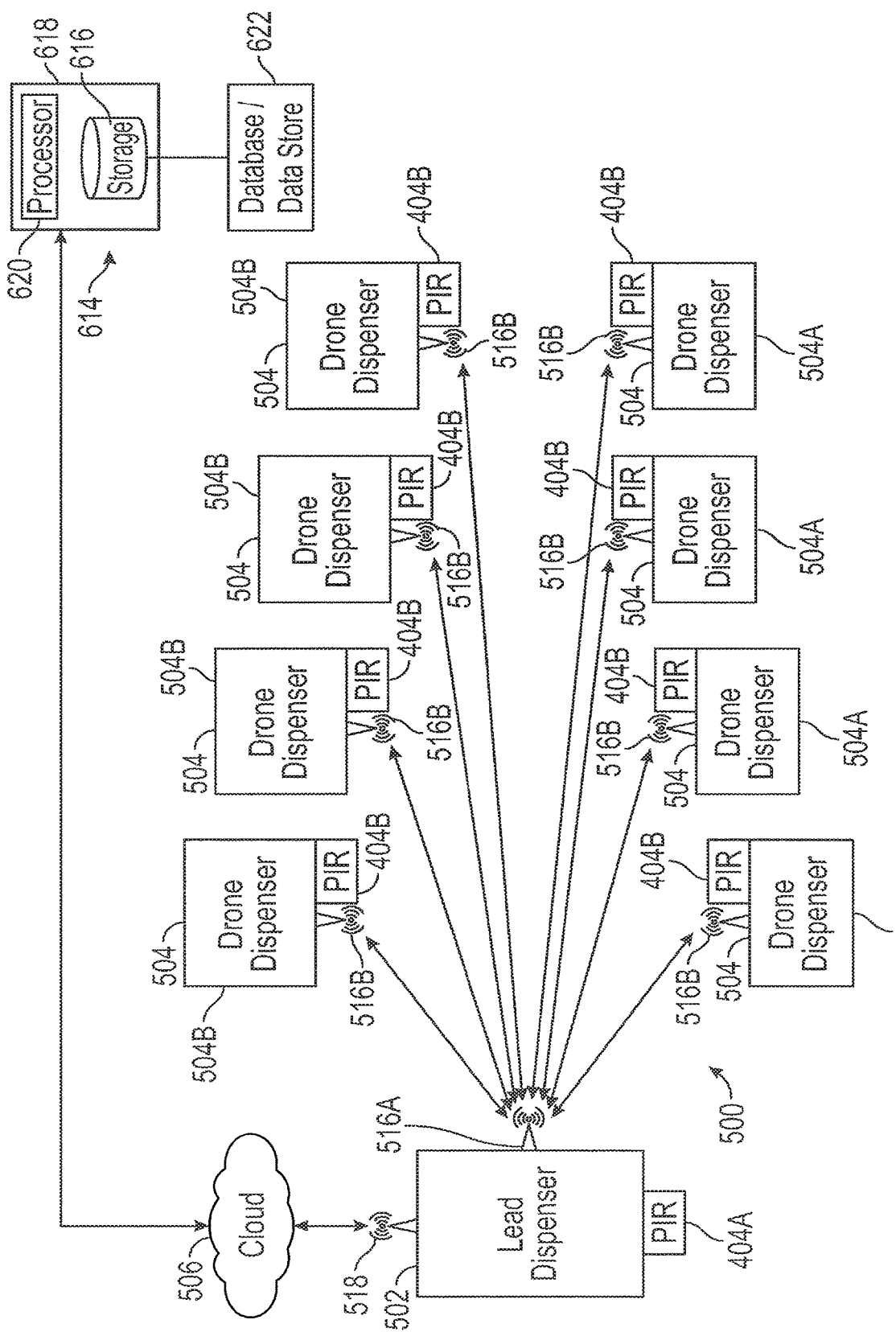
FIG. 7 shows a schematic view of a monitoring and dispensing system including a lead dispenser and a plurality of drone dispensers according to principles of the present disclosure.

FIG. 7 shows an example embodiment of a dispensing system 500 according to principles of the present disclosure. The dispensing system 500 generally can include a dominant or lead dispenser 502 and a plurality of drone or follower dispensers 504 in communication with the lead dispenser 502. The plurality of drone dispensers 504 can include one or more liquid dispensers 504A, such as soap dispensers, hand sanitizer dispensers, etc. and/or one or more sheet material dispensers 504B, such as tissue dispensers, paper towel dispensers, etc. The lead dispenser 502 can include a sheet material dispenser (e.g., tissue dispensers, paper towel dispensers, etc.) or a liquid dispenser (e.g., a soap dispenser or a hand sanitizer dispenser).

The lead dispenser 502 further can be in communication with a network 506, such as cloud based network or other suitable public (e.g., the Internet) or private network, and the lead dispenser 502 can provide one or more signals, packets, etc. including, or otherwise related to, dispenser information and/or alerts, notifications, etc., generated by the lead dispenser 502 and the drone dispensers 504 to the network 506 for access by a system operator, maintained personnel, etc. The dispenser information can include information related to power levels (e.g., battery levels), supply levels (e.g., information related to remaining amounts of sheet material or liquid), usage (e.g., times and dates of when the dispenser was used, amounts the dispenser was activated during a specific time period, other usage rates or statistics, etc.) The alerts, notifications, etc. can be generated, e.g., if the dispensers 502/504 are experiencing a low power, low supply, error states, etc.

Figure 8A:
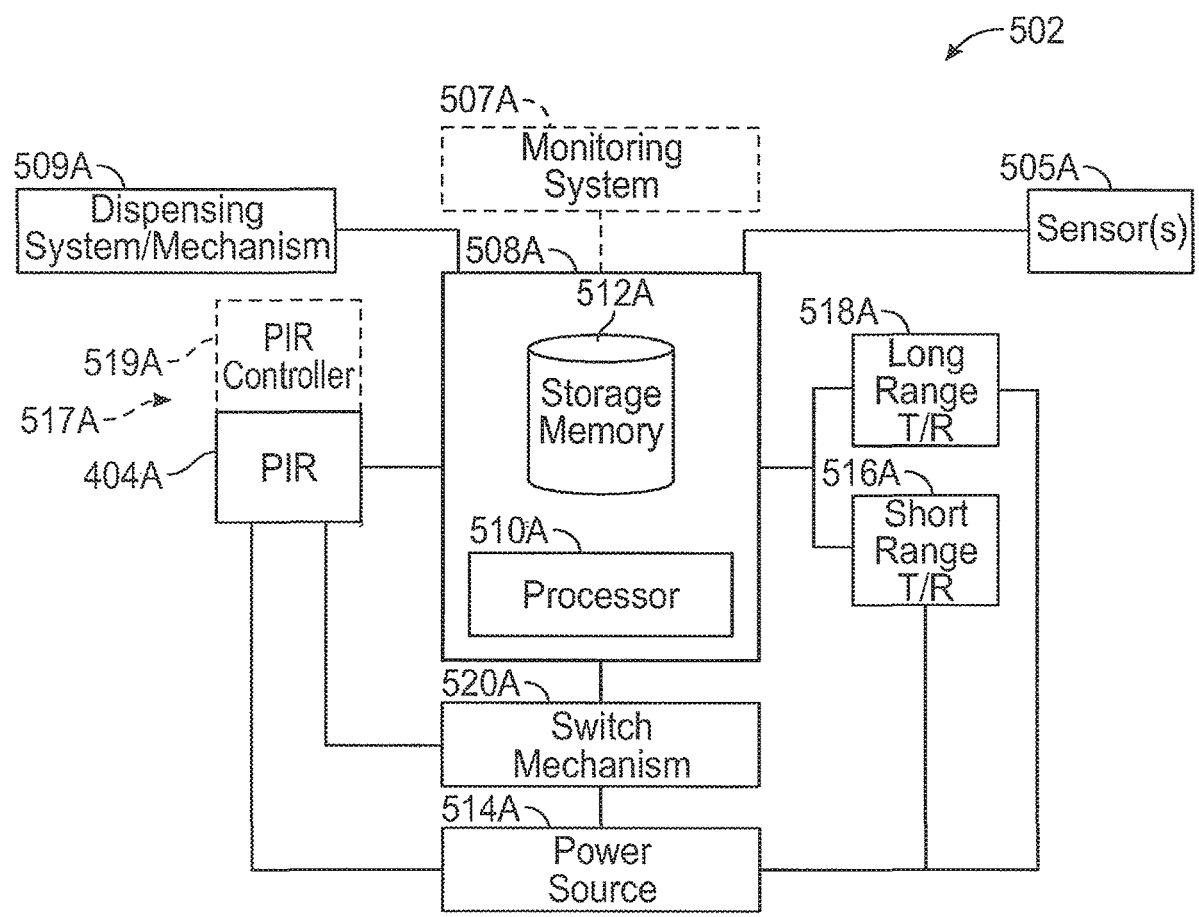
FIGS. 8A and 8B show a circuit diagrams for the lead dispenser and a drone dispenser according to various aspects of the present disclosure.
Figure 8B:
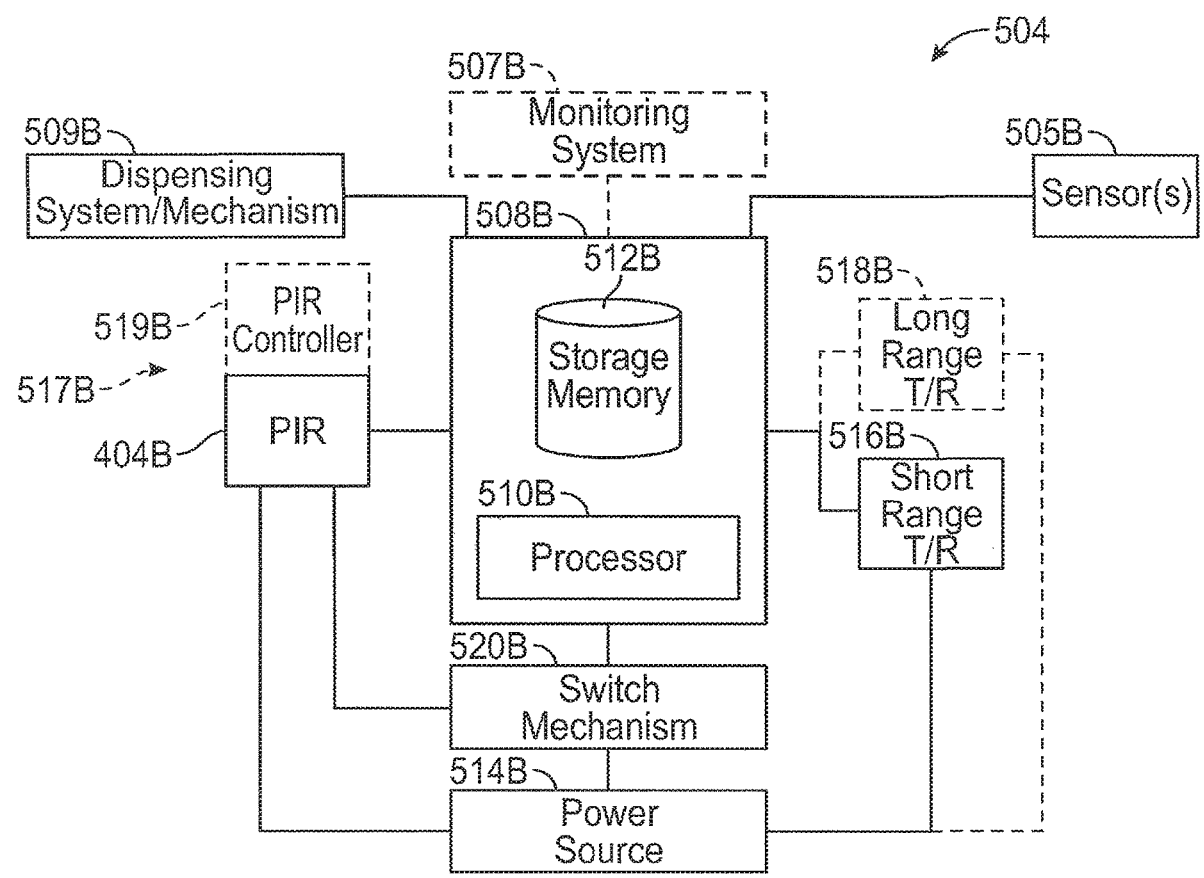

FIGS. 8A and 8B are schematic diagrams illustrating the lead dispenser 502 and drone dispensers 504, respectively. As shown in FIGS. 8A and 8B, the lead dispenser 502 and the drone dispensers 504 each include a dispenser controller or control unit 508A/508B that controls various operations/functions of the lead dispenser 502 and drone dispensers 504. Each dispenser controller 508A/508B of the dispensers 502/504 generally can include a printed circuit board assembly ("PCBA") with a processor 510A/510B, such as a micro-processor, CPU, etc., and one or more data stores or memories 512A/512B, such as RAM, ROM, or other non-volatile memories. Each dispenser controller 508A/508B further can be connected to or otherwise communicate with other components of the dispensers 502/504, such as sensors 505A/B, e.g., proximity sensors 28/310, paper detection sensors, personnel tracking sensors, etc.; optional monitoring systems 507A/B; drive systems or dispensing systems 509A/B, such as motor driven feed rollers 74, fluid pumps 308, etc.; or other suitable components of the dispensers 502/504.

The data stores 512A/512B can store instructions, workflows, etc. that can be accessed and executed by the processor 510A/510B to facilitate operations of the dispensers 502/504 (e.g., for dispensing of sheet material or liquid therefrom, for monitoring usage of the lead dispenser 502, such as operating a monitoring system 507A/B thereof that determines a remaining amount of sheet material or liquid, for communicating with and/or controlling the drone dispensers 504, etc.). The data stores 512A/512B further can store dispenser information generated by the respective dispensers 502/504, and one or more data stores 512A of the lead dispenser 502 can store dispenser information received from the drone dispensers 504.

In addition, as generally shown in FIGS. 8A and 8B, the lead dispenser 502 and drone dispensers 504 each include a power source 514A/514B, such as one or more batteries, an alternating current (AC) distribution system of a facility, or other AC or direct current (DC) power sources. The lead dispenser 502 and drone dispensers 504 will include a short-range receiver/transmitter 516A/516B, such as a Bluetooth® or other suitable RF or short-range signal receiver/transmitter, to facilitate communication between the lead dispenser 502 and the drone dispensers 504 (FIG. 7).

The lead dispenser 502 (FIG. 8A) also can include an additional, long-range receiver/transmitter 518A, such as a narrowband ("NB") receiver/transmitter (e.g., 4G, LTE, 5G, etc.) or other suitable transmitter/receiver, e.g., Wifi, for transmitting and/or receiving information to/from or otherwise communicating with the network 506 (FIG. 7). Further, in some variations, the drone dispensers 504 can have an identical construction to the lead dispenser 502 and will include a long-range receiver/transmitter 518B, such as a narrowband ("NB") receiver/transmitter (e.g., 4G, LTE, 5G, etc.) or other suitable transmitter/receiver, e.g., Wifi, etc. In these variations, the long-range transmitter/receivers 518B of one or more of the drone dispensers 504 can be deactivated or generally maintained in a low power state.

As further indicated in FIGS. 7-8B, the lead dispenser 502 and drone dispensers 504 each can include a passive infrared radiation (PIR) sensor 404A/404B configured to detect infrared radiation of a person or people (e.g., that is indicative of the presence or movement of individuals within a prescribed detection range, area, zone, etc. covered by each of the PIR sensors 404A/404B around their respective dispensers 502/504). PIR sensors 404A/404B can be in communication with the dispenser controller 508A/508B of their respective dispensers 502/504, which dispenser controller 508A/508B can be deactivated and activated based upon/responsive to signals received from corresponding PIR sensors 404A/404B (FIGS. 8A and 8B).

In particular, when the PIR sensors 404A/404B detect infrared radiation from a person or persons (e.g., indicating an occupied state or mode), their respective dispenser controllers 508A/508B and other dispenser components in communication therewith, such as sensors 505A/B, monitoring systems/sensors 507A/B, drive or pumping mechanisms 509A/B, etc., can be connected to or otherwise placed in communication with their corresponding power source 514A/514B so as to receive power/current therefrom. When the PIR sensors 404A/404B do not detect infrared radiation from a person or people (e.g., indicating an unoccupied state or mode), their respective dispenser controllers 508A/508B and other dispenser components in communication therewith can be placed in a low or minimal power state and disconnected from the power source 514A/514B such that no power/current is provided to the dispenser controller 508A/508B such that the dispenser controller 508A/508B and other dispenser components in communication therewith are deactivated and do not draw or consume power from the power source 514A/514B. That is, in the low or minimized power state, only the sensors 404A/404B will draw or consume power from the power source 514A/514B.

In one exemplary construction, as shown in FIGS. 8A and 8B, each of the lead dispenser 502 and drone dispensers 504 also can include a switch mechanism or circuitry 520A/520B, e.g., including an NPN triode or other, similar mechanism that can block or shut off power to the dispenser controllers 508A/508B. The switch mechanism 520A/520B will be in communication with the sensors 404A/404B to disconnect and connect the dispenser controller 508A/508B (and other dispenser components in communication therewith) from/to the power source 514A/514B in the unoccupied and occupied modes, respectively. For example, in the unoccupied mode (e.g., when the sensor 404A/404B does not detect infrared information from a person or people), the sensors 404A/404B can output one or more signals, e.g., a low level signal, to their respective dispenser controllers 508A/508B. Upon receipt of this low level signal, the dispenser controllers 508A/508B, e.g., the processor 510A/510B, can determine that the sensors 404A/404B are in the unoccupied mode, and the dispenser controllers 508A/508B can initiate a shutdown or power down sequence. In some embodiments, the switch mechanisms 520A/520B can be incorporated with the PCB of their associated dispenser controller 508A/508B; though the switch mechanisms 520A/520B otherwise be connected to or in communication with their dispenser controllers 508A/508B.

In some aspects, the dispenser controllers 508A/508B (and other dispenser components in communication therewith) can finish or complete any on-going work, functions, operations, etc. thereof and generate and transmit one or more command signals to place the short-range transmitter/receivers 516A/516B (as well as the long-range transmitter/receiver 518) into a low power/power off state. As the dispenser controller 508A/508B enters into its power down sequence, the dispenser controller 508A/508B can generate and output one or more signals, e.g., a low level signal, to the switch circuitry 520A/520B such that the switch circuitry 520A/520B is in an open or "off" state, disconnecting the power sources 514A/514B from their associated dispenser controllers 508A/508B to completely shut down/power off the dispenser controllers 508A/508B and substantially all other components of the dispensers 502/504, except for the sensors 404A/404B, and, in some variations, the short-range 516A/516B and long-range 518A/518B transmitter/receivers. In these variations, the transmitters/receivers 516A/516B and 518A/518B can be placed in a low power or sleep state. In this regard, the dispenser controller 508A/508B and substantially all other components of the dispensers 502/504 (e.g., sensors 505A/B, optional monitoring systems 507A/B, dispensing systems 509A/B, etc.) generally are decoupled from the power sources 514A/514B such that the dispenser controllers 508A/508B and other operative components of the dispensers 502/504 do not consume or draw power from the power sources 514A/514B while in such low/minimal power state.

The dispenser controllers 508A/508B can be powered on when their respective sensors 404A/404B capture infrared radiation from a person or persons and are in the occupied state. In particular, when one of the sensors 404A/404B captures infrared radiation of a person or persons to indicate an occupied mode, that sensor 404A/404B will output one or more signals, e.g., a high level signal, to its corresponding or associated switch circuitry 520A/520B to place such switch circuitry 520A/520B in a closed or "on" state to couple or re-establish communication between the power source(s) 519A/B and the dispenser controllers, and thus provide power to the dispenser controllers 508A/508B from the power source 514A/514B to place the dispenser controllers in an operative state for enabling dispensing operations. In addition, the dispenser controllers 508A/508B further can generate and provide one or more signals to activate or wake up the short-range transmitter/receivers 516A/516B and/or long-range transmitter/receivers 518A/518B, e.g., as needed, when powered on.

In some variations, a timer, time clock, timing circuit, etc. can be integrated with one or more of the sensors 404A/404B to delay the shutdown sequence of the dispenser controllers 508A/508B. For example, when the sensors 404A/404B do not detect the presence of a person, the timer can be activated, and upon expiration of the timer, the sensors 404A/404B can transmit the signals to their respective dispenser controller 508A/508B to initiate their shutdown sequence. The timer can be set to any suitable time period, such as about 30 seconds, about 1 minute, about 5 minutes, about 10 minutes or other suitable time periods.

Additionally, in some embodiments, the lead and/or drone dispensers 502 and 504 optionally can include a smart PIR sensor 517A/517B. The smart PIR sensor of the lead and/or drone dispensers can include a PIR controller 519A/519B, such as a mini-CPU or low power CPU or any other suitable computing or processing unit than consumes or draws minimal power (e.g., between about 20 μA to about 25 μA and as low as about 10 μA), that is integrated with or otherwise in communication with the PIR sensors 404A and 404B. In one embodiment, the PIR controllers 519A/B and the PIR sensors 404A/404B can be part of a printed circuit board assembly ("PCBA"); though the PIR controller 519A/B and the PIR sensors 404A/404B can be otherwise electrically connected or otherwise in communication without departing from the scope of the present disclosure.

The PIR controllers 519A/519B further can be in communication with the switch mechanisms 520A/520B and/or the dispenser controllers 508A/508B, and can generate one or more signals responsive to captured or detected radiation of the PIR sensors 404A/404B (i.e., depending on whether such PIR sensors 404A/404B are in an occupied or unoccupied state). That is, when each PIR controller 519A/519B determines that its corresponding PIR sensor 404A/404B does not capture radiation, i.e., is in the unoccupied state, each PIR controller 519A/519B can transmit one or more signals to its corresponding dispenser controller 508A/508B and/or switch mechanism 520A/520B to place the dispenser 502/504 in the low or minimal power state, and when each PIR controller 519A/519B determines that its corresponding PIR sensor 404A/404B captures infrared radiation, the PIR controller 519A/519B can generate and transmit one or more signals to its corresponding switch mechanism 520A/520B and/or dispenser controller 508A/508B to place the dispenser 502/504 to place the dispenser 502/504 in the "on" or full power state.

In particular, according to one embodiment, when the PIR sensors 404A/404B detect the presence of one or more individuals, the PIR controllers 519A/519B will receive one or more high level signals from their PIR sensors 404A/404B. Upon receipt of these high level signal(s), the PIR controllers 519A/519B will output one or more high level signals to their corresponding dispenser controllers 508A/508B and/or the switch mechanisms 520A/B for powering on the dispenser controllers 508A/508B. Furthermore, when the PIR sensors 404A/404B do not detect the presence of any individuals, the PIR controllers 519A/519B will receive one or more low level signals from the PIR sensors 404A/404B. Upon receipt of these low level signal(s), the PIR controllers 519A/519B will output one or more low level signals to the dispenser controllers 508A/508B to initiate a shutdown sequence and allow the dispenser controllers 508A/508B to finish any ongoing work/processes or other work/processes as necessary. When the work/processes of the dispenser controllers 508A/508B are complete, the dispenser controllers 508A/508B can output one or more low level signals to indicate that its work is complete, and thereafter the PIR controllers 519A/519B can output one or more signals to deactivate the dispenser controllers 508A/508B (e.g., the PIR controllers 519A/519B can output one or more signals to the switch mechanisms 520A/520B to decouple/disconnect the dispenser controllers 508A/508B and the power sources 514A/514B or the PIR controllers 519A/519B can output one or more signals to the dispenser controllers 508A/508B to disconnect/decouple the dispenser controllers 508A/508B and the power sources 404A/B or to otherwise deactivate/power down the dispenser controllers 508A/508B). That is, the dispenser controllers 508A/508B generally remain coupled to their corresponding power sources 514A/514B or activated until the PIR controllers 519A/B receives the low level signal(s) therefrom to indicate that necessary work is complete and the dispenser controllers 508A/508B can be safely decoupled from power or otherwise deactivated. The PIR controllers 519A/519B further can output one or more high level signals to help to insure stability of the dispenser controllers 508A/508B.

In some variations, each PIR controller 519A/519B can include one or more timers, which can be initiated after the PIR controllers 519A/519B are initially placed in their unoccupied state. Thereafter, until the expiration of the timer(s), the PIR controller 519A/519B will not decouple the dispenser controllers 508A/508B from the power source 514A/514B or otherwise deactivate the dispenser controller 508A/508B. Such timers can be set at varying time intervals (e.g., based on time of day/usage period, usage history, or other factors) to help reduce unnecessary cycling power off/power on cycles). For example, during peak usage times, a longer timer can be used before shut down/powering down of the dispensers, while at night, when usage is lower, a shorter timer period can be used.

In alternative constructions, the switch mechanism 520A/520B can be omitted, and when the PIR sensor 404A/404B is determined to be in the unoccupied state, the PIR controller 519A/519B can generate one or more signals to the dispenser controller 508A/508B to initiate a shutdown or power down sequence, such that the dispenser controller 508A/508B and other operative dispenser components in communication therewith shut down/shut off and consume minimal or no power from the power source 514A/514B. Then, when the PIR sensor 404A/404B is in the occupied state, i.e., captures infrared radiation, the PIR controller 518A/519B can transmit one or more control signals to the dispenser controller 508A/50B to initiate a start-up sequence of the dispenser controller 508A/508B.

The PIR controller 519A/519B can consume between less than about 25 µA to less than about 10 µA, e.g., in one embodiment, less than about 12 µA, while the PIR sensor 404A/404B can consume between less than about 20 µA to less than about 10 µA, e.g., in one embodiment, less than about 12 µA. Accordingly, with embodiments of the present disclosure, in the low/minimal power state, the dispensers 502/504 can consume less than about 45 µA, less than about 44 µA, less than about 43 µA, less than about 42 µA, less than about 41 µA, less than about 40 µA, less than about 39 µA, less than about 38 µA, less than about 37 µA, less than about 36 µA, less than about 35 µA, less than about 34 µA, less than about 33 µA, less than about 32 µA, less than about 31 µA, or less than about 30 µA, less than about 29 µA, less than about 28 µA, less than about 27 µA, less than about 26 µA, less than about 25 µA, less than about 24 µA, less than about 23 µA, less than about 22 µA, less than about 21 µA, and/or less than about 20 µA, or lower amounts without departing from the scope of the present disclosure.

In addition, upon activation of the lead dispenser 502 and/or the drone dispensers 504, e.g., when the sensors 404A/404B of the dispensers 502/504 are in the occupied state, the dispenser controllers 508A/508B of the dispensers 502/504 can be activated (i.e., connected to the power source 514A/514B), and may log, generate, and store dispenser information related to operations/functions of the dispensers 502/504. For example, the lead 502 and drone dispensers 504 can generate dispenser information, e.g., including time and date information, when the dispensers 502/504 are activated, and can store the dispenser information in the one or more data stores 512. The lead dispenser 502 and drone dispensers 504 further can generate, record, etc., additional dispenser information, such as voltage usage, power levels, paper or liquid levels, usage statistics, etc. and/or other suitable dispenser information, which also can be stored in the data store(s) 512.

The drone dispensers 502 generally transmit the dispenser information to the lead dispenser 502 each time the drone dispensers 504 are activated (i.e., each time the sensor 404 of the drone dispensers is in the occupied stated); however, in the alternative, the drone dispensers 504 can provide the dispenser information to the lead dispenser 504 periodically, e.g., the drone dispensers 504 can provide the dispenser information to the lead dispenser 504 after a prescribed number of activations, e.g., every five, ten, twenty, fifty, etc., activations, or the drone dispensers 504 can provide the dispenser information after a certain time period, a certain time in the day, etc.

The lead dispenser 502 stores the dispenser information received from the drone dispensers 504 (and generated by the lead dispenser 502) in the data stores 512A, and transmits signals, packets, etc., including or related to the dispenser information to the network 506. The lead dispenser 502 may transmit signals/packets including the dispenser information each time the lead dispenser 502 is activated (e.g., when the sensor 404A is in an occupied state). However, alternatively, the lead dispenser 502 can transmit the signals/packets including the dispenser information to the network 506 periodically, such as after a certain number of activations of the sensor 404, e.g., ten, twenty, thirty, forty or more activations thereof, though the lead dispenser 502 also can transmit the signals/packets including the dispenser information after a certain time period, a certain time in the day, etc. without departing from the present disclosure.

The dispenser information provided to the network 506 can be accessed by system operators, maintenance personnel, etc. and further can be processed, e.g., for tracking or mapping the movements of individuals throughout a facility including the dispenser system 500, for optimizing usage of the lead dispenser 502 and/or the drone dispensers 504, for maintenance or servicing of the lead dispenser 502 and/or the drone dispensers 504, etc.

The drone dispensers 504 further can generate and transmit alerts, notifications, etc., to the lead dispenser 502. For example, if one of the drone dispensers 504 is running low on sheet material or a liquid supply (e.g., as determined by one or more monitoring systems of the drone dispensers 504), is experiencing an error condition, such as a jam, component failure, etc., the drone dispenser 504 can generate and transmit and an alert to the lead dispenser 502 (i.e., using the short-range transmitter/receiver 516B). Upon receipt of the alert, the lead dispenser 502 may generate and transmit one or more signals or information packets including information related to the alert to the network 506 (using the long-range transmitter/receiver 518A/518B) to notify a system operator, maintenance provider, etc. of the alert e.g., so they can refill, replace the batteries, or otherwise service the drone dispenser 504.

The lead dispenser 502 further can generate and transmit alerts, notifications, etc. to the network (e.g., if the lead dispensers 502 is running low on sheet material or liquid supply, such as determined by one or more monitoring systems of the lead dispenser 502; is experiencing an error condition, such as a jam or a component failure; etc.). The alerts, notifications, etc. generally can be sent to the lead dispenser 502 and to the network 506 immediately or soon after the condition that led to generation of the alert, notification, etc.

The drone dispensers 504 further can continuously generate and transmit signals to the lead dispenser 502 when the sensors 404B of one or more of the drone dispensers 404 are in the occupied mode. For example, the drone dispensers 504 can transmit one or more signals, using the short range transmitter 516B thereof, to the lead dispenser 502 at a prescribed interval, e.g., about every 1 second, about every 10 seconds, about every 30 seconds, etc., when in the sensor 404B is in the occupied mode.

According to the present disclosure, the lead dispenser 502 generally remains in the on/active/full power state (i.e., with the dispenser controller 508A/508B and other dispenser components in communication therewith connected to/coupled with the power source 514A/514B) when one or more of the sensors 404B of one or more of the drone dispensers 504 are in an occupied state. That is, the lead dispenser 502 remains in the on state when signals are received from one or more of the drone dispensers 504 even if the sensor 404A of the lead dispenser 504 is in the unoccupied mode. Furthermore, the lead dispenser 502 can remain in the active/on state (i.e., with the dispenser controller 508A connected to/couple with the power source 514A) for a prescribed time period after the sensor 404A of the lead dispenser 502A and all of the sensors 404B of the drone dispensers 504 are in an unoccupied state (e.g., when no one is within a prescribed proximity to the lead 502 or drone 504 dispensers).

The prescribed time period can be set by the operator of the system and can include, but is not limited to, approximately five minutes, approximately ten minutes, approximately thirty minutes, approximately one hour, etc. or other suitable time period without departing from the scope of the present disclosure. Accordingly, when the dispenser controller 508A of the lead dispenser 502 determines that all of the sensors 404B of the corresponding drone dispensers 504 are in the unoccupied mode (e.g., when the short-range transmitter 516A of the lead dispenser fails to receive signals from the drone dispensers 502) and the sensor 404A of the lead dispenser 502 also is in an unoccupied mode, the dispenser controller 508A may initiate a timer, and upon expiration of the timer, the dispenser controller 508A can initiate the dispenser controller 508A power down sequence described above.

In some variations, the lead dispenser 502 can generate and transmit one or more signals to activate one or more of the plurality of drone dispensers 504 upon activation of the lead dispenser 502, e.g., when the sensor 404 of the lead dispenser 502 is in an occupied mode; however, all of the drone dispensers 504 can remain off/deactivated until their sensor 404B is in the occupied mode, without departing from the scope of the present disclosure. Furthermore, in some variations, the sensors 404B of the drone dispensers 504 can be disconnected from the power source 514B when the lead dispenser 502 is in the power down mode (and can be powered on when the transmitter/receiver 516B receives one or more signals from the lead dispenser 502).

In addition, in some variations, the lead dispenser 502 can be activated when a signal is received by the long-range transmitter/receiver 518A/518B, e.g., when a system operator, maintenance personnel, etc., want to access the dispenser information of the lead dispenser 502 or one or more of the drone dispensers 504. The lead dispenser 502 further can be activated when a signal is received from one or more of the drone dispensers 504, e.g., via the short-range transmitter 516A (or in the long-range transmitter in the case one is included with one or more of the drone dispensers 504.

Figure 9A:
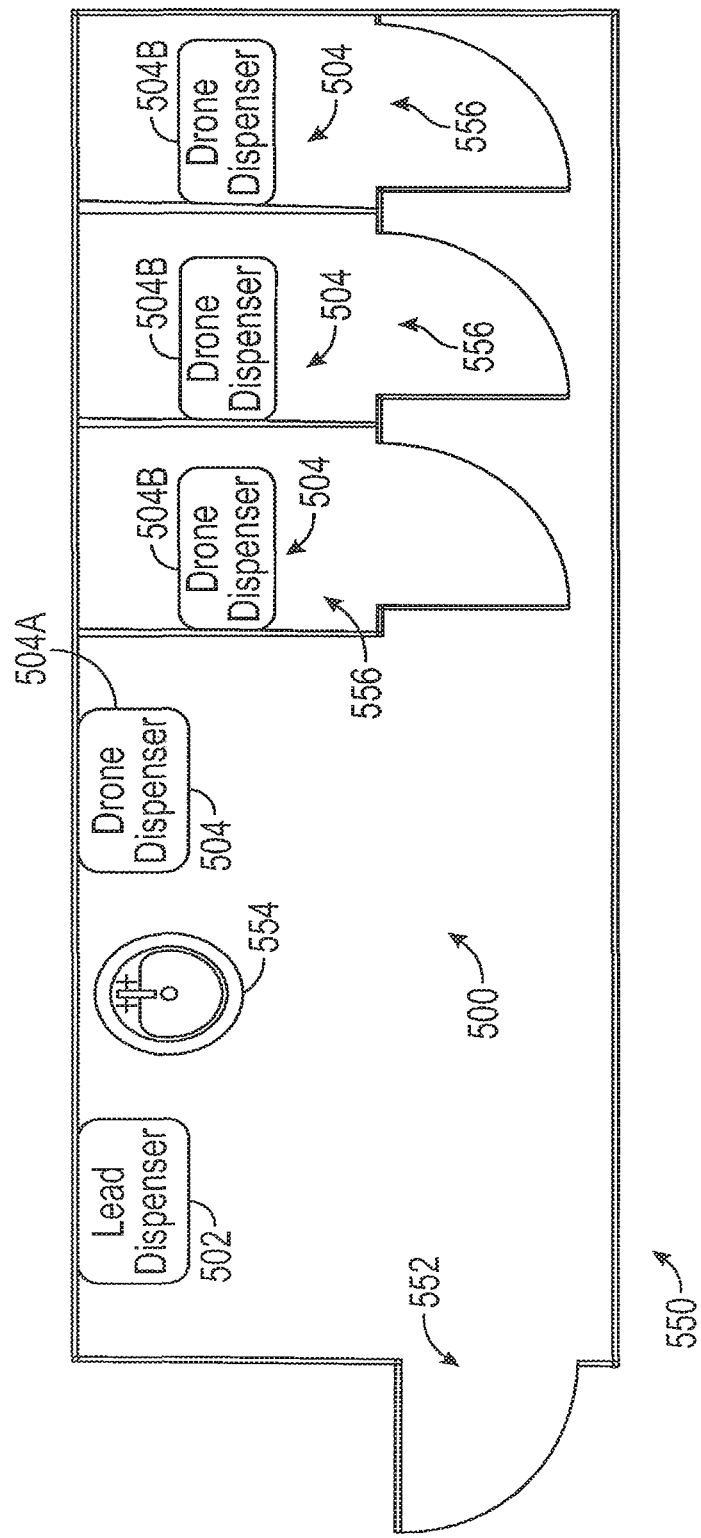
FIGS. 9A and 9B show exemplary facilities including a dispensing system such as shown in FIG. 7.
Figure 9B:
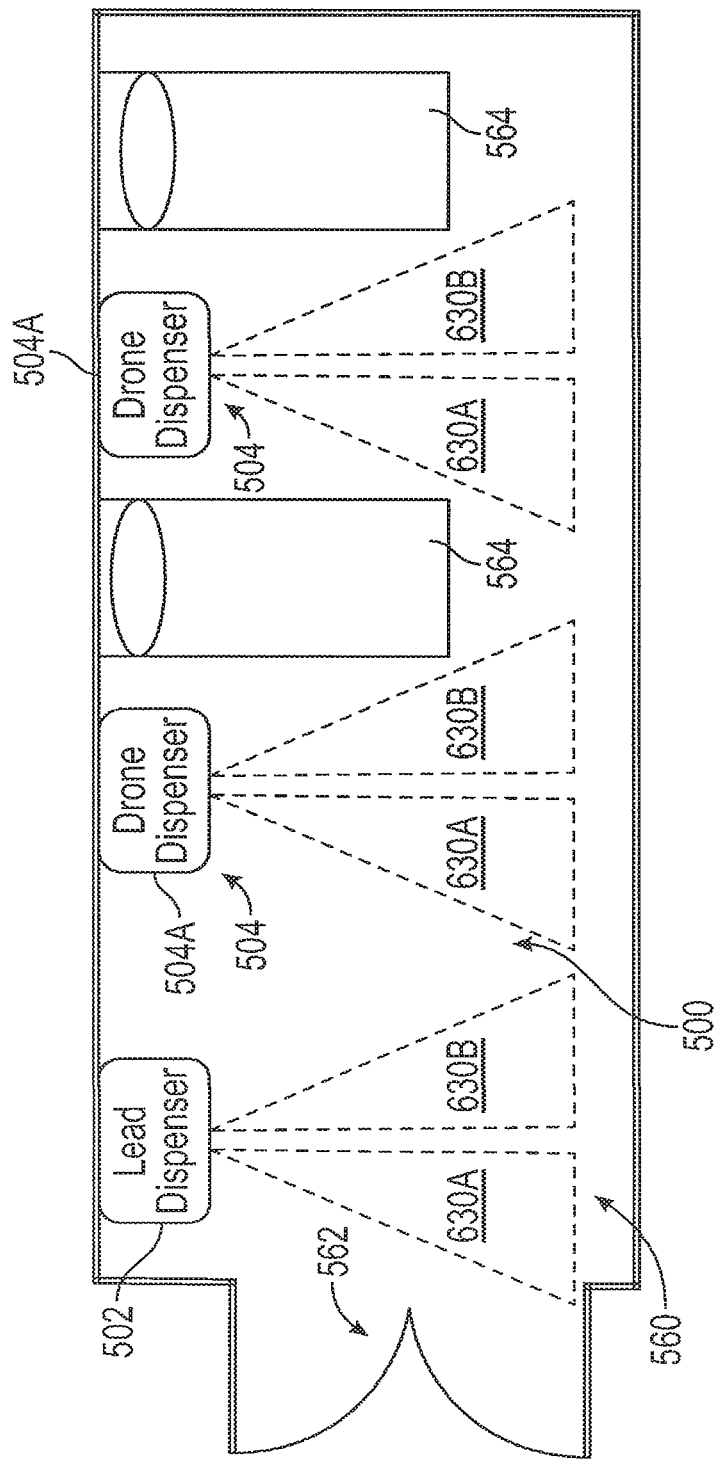

As generally shown in FIGS. 9A and 9B, the dispensing system 500, including a lead dispenser 502 and a plurality of drone dispensers 502 can be placed at various locations within a facility, such as within a restroom 550 of the facility (FIG. 9A), or within hospital rooms 560 (FIG. 9B).

By way of example, and as shown in FIG. 9A, a lead dispenser 502, which can include a sheet material dispenser, can be placed at, near, or substantially proximate to an entry 552 to a restroom 550 (e.g., such that the sensor 404A of the lead dispenser 502 is in the occupied mode when a person or persons enter the restroom 550). The plurality of drone dispensers 504 can include a liquid dispenser 504A positioned substantially near a sink or faucet 554 of the restroom 500, and further can include a plurality of tissue dispensers 504B placed within the various stalls 556 of the restroom 550.

The lead dispenser 502 can be activated when an individual(s) enters the restroom 550, and the tissue dispensers 504B further can be activated and generate and transmit one or more signals to the lead dispenser 502 when the individual enters one of the stalls 556. When the individual exits the stall 556, the tissue dispenser 504B can be deactivated. The liquid dispenser 504A can be activated when the individual approaches the sink 554, e.g., to wash their hands or to user the liquid dispenser 504A, and deactivated after the individual moves sufficiently away from the liquid dispenser 504A. If the liquid dispenser 504A and/or the tissue dispensers 504B are running low on paper, have a low power supply, or are experiencing an error condition, the dispensers 504A/504B can generate and transmit an alert, notification, etc. to the lead dispenser 502 to be transmitted to the network 506 to notify system operators, maintenance personal, etc.

The lead dispenser 502 generally can remain activated while an individual is in the restroom 550, with the lead dispenser 502 receiving signals from the tissue 504B and/or liquid dispensers 504B. The lead dispenser 502 further can receive dispenser information from the dispensers 504A/504B related to the movements/activities of the individual (e.g., the particular dispensers activated and/or used and the time and date when they were used) and provide that dispenser information as well as any dispenser information generated by the lead dispenser 502 to the network 506 for processing, e.g., to track or map movements of the individual in the restroom, activities of the individual within the restroom (e.g., to determine if the individual washed their hands after using a stall), etc.

After the individual exits the restroom and no other individuals or activity are detected in the restroom, the lead dispenser 502 can be deactivated, i.e., its dispenser controller 508A and dispenser components in communication therewith can be disconnected from the power source 514A, as can be the drone dispensers 504 linked thereto. As a result, when the restroom 550 is unoccupied, the power consumed by the dispenser system 500 in the restroom 550 is substantially reduced, e.g., with the dispenser controller 508A/508B and substantially all other operative components of the dispensers 502/504 disconnected from the power sources 514A/514B, except for the sensors 404A and 404B and the long-range 518A and short-range receivers 516A and 516B, which remain active and in a low power or sleep state.

As shown in FIG. 9B, the dispenser system 500 also can be integrated within a hospital room 560. For example, the lead dispenser 502 can include a sheet material dispenser or a liquid (e.g., hand sanitizer) or other type dispenser positioned to be substantially adjacent, proximate, etc. an entry 562 of the hospital room 560 or otherwise positioned, arranged, oriented, etc. so that the sensor 404A of the lead dispenser 502 is in the occupied mode when a person or persons enter the hospital room 560. The drone dispensers 504 can include liquid dispensers 504A, such as soap or sanitation dispensers, positioned about the hospital room 560, or other type dispensers. For example, the drone dispenser 504 can be position to be substantially adjacent, proximate, or otherwise near a hospital bed 564 in the hospital room 560.

Accordingly, when one or more individuals enter the hospital room 560 the lead dispenser 502 can be activated (e.g., with the sensor 404A in the occupied mode, the dispenser controller 508A of the lead dispenser 502 can be connected to the power source 514A). In addition, the drone dispensers 504 can be activated when individuals in the hospital room 560 are within a certain proximity of the drone dispensers 504, e.g., as/when the individuals approach the hospital beds 564 and/or the dispensers 504. The lead dispenser 502 and the drone dispensers 504 further can generate, log, store, etc. dispenser information (e.g., times and dates of when the dispensers 502/504 where activated, whether the individuals used the dispensers 502/504, etc.). The drone dispensers 504 can transmit dispenser information and/or one or more alerts, notifications, etc. (e.g., if a lower power, low supply, error, etc., state is detected), and the lead dispenser 502 can transmit dispenser information/ alerts received from the drone dispensers 504 and generated by the lead dispenser 502 to the network 506 for processing thereof, e.g., for tracking usage of the dispensers 502/504, for maintenance of the dispensers 502/504, and/or for tracking or mapping movements or other activities of the individuals within the hospital room 560, etc.

When the sensors 404B of the drone dispensers 504 are in the unoccupied state, the drone dispensers 504 are placed in the low/minimal power state (i.e., with the power source 514B disconnected from the dispenser controller 508B and other operative dispenser components in communication therewith). And, when all of the sensors 404A and 404B of the lead dispenser 502 and the drone dispensers 504 are in the unoccupied state, the lead dispenser 502 is placed in the low/minimal power state (i.e., with the power source 514A disconnected from the dispenser controller 508A and other operative dispenser components in communication therewith) after a prescribed time period, such as approximately 5 minutes, approximately 10 minutes, etc. As a result, when the hospital room 560 is unoccupied, the power consumed by the dispenser system 500 in the hospital room is substantially reduced, e.g., with the dispenser controller 508A/ 508B and substantially all other power consuming components of the dispensers 502/504 being disconnected from the power sources 514A/514B, except for the sensors 404A and 404B and the long-range 518A and short-range receivers 516A and 516B in a low power or sleep state.

Figure 10A:
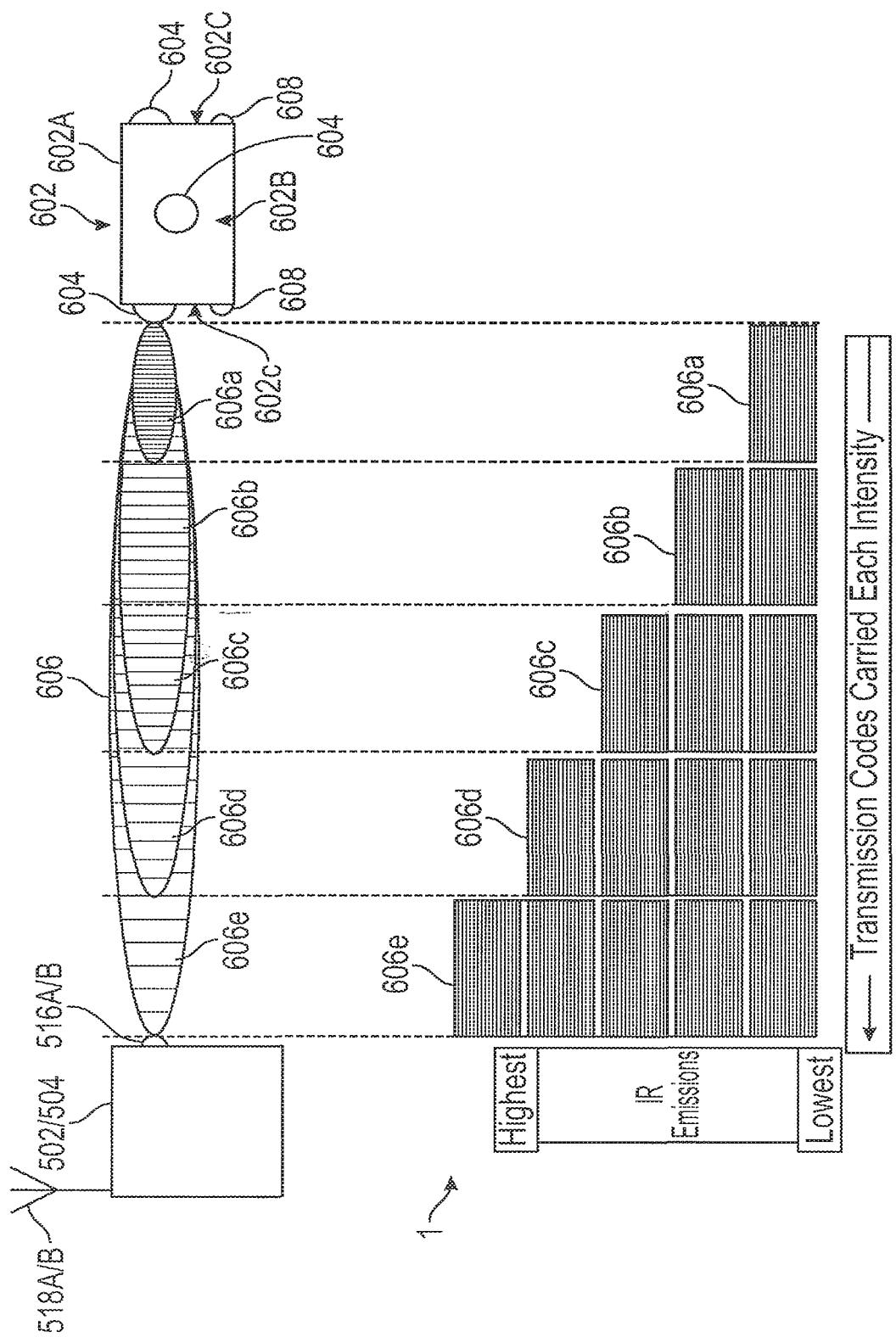
FIG. 10A illustrates schematic view of an exemplary badge transmitting a series of signals communicated to lead or drone dispensers configured to receive these signals according to one aspect of the present disclosure.
Figure 11:
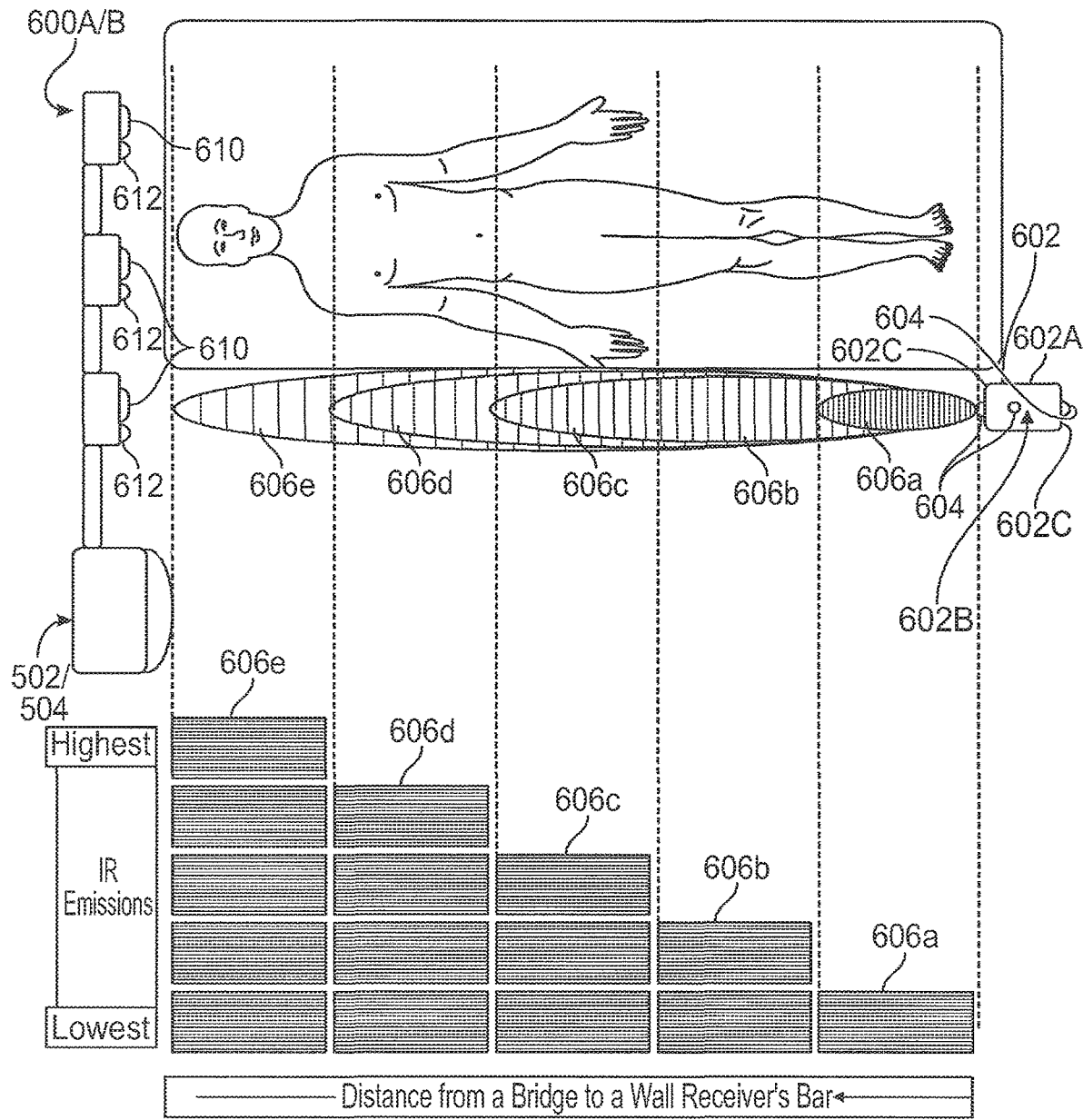
FIG. 11 provides an overview example of a badge transmitting signals to a series of primary receivers disposed near the head of a patient bed according to one example.

As FIGS. 10A-10B and 11 indicate, the lead dispenser 502 and the drone dispensers 504 further can communicate with devices 602, such as badges, fobs, key cards, etc. or other passive or active devices, carried by personnel throughout the facilities 550/560 or other suitable facility. The badges 602 can be carried or worn by various persons or personnel, such as medical workers or patients in a hospital or medical facility 560, by employees of a restaurant, or other facilities with bathrooms 550 and/or where compliance with sanitary or similar protocols and procedures is necessary. The badges 602 also can communicate with the lead 502 or drone dispensers 504 (e.g., via the short-range transmitters/receivers 516A/516B of the lead dispenser 502 and the drone dispensers 504 (FIG. 10A) and/or using separate monitoring sensor assemblies 600A/B (FIG. 10B-10C)) positioned at desired locations within preselected areas or environments throughout the selected facility (e.g., on or near the walls, doorframes, patient beds, washing stations, sinks, toilets, or any other locations or areas in a facility where sanitizing or disinfecting actions are required and/or treatment or care to patients is provided).

The locations of the lead 502 or drone dispensers 504 generally will be known, such as when mounted to a patient bed, so as to be linked or associated with a known bed/ patient identifier for coordinating the location tracking/ mapping of the badges detected thereby. The lead dispenser 502 and drone dispensers 504 further can generate, log, store, transmit, etc. device information based on the signals transmitted to or received from the carried badges. In one aspect, the drone dispensers 504 can transmit the generate/ stored device information to the lead dispenser 502, and the lead dispenser can transmit the device information to the network 506 for processing thereof, e.g., for tracking or mapping activities or movements of the hospital personnel carrying the devices, for monitoring compliance with sanitation procedures, etc.

FIGS. 10A-10B and 11 indicate that each badge 602 can transmit a plurality of beams or signals 606 that can be received or otherwise detected by one or more of the lead 502 or drone dispensers 504. Based on such signals 606, the location, proximity, or range of each badge 602 with respect to the dispenser(s) that receive its signals, and a specific transmitter signature or other identifier associated with each badge 602 can be detected and captured by one or more of the lead 502 and/or drone dispensers 504. The badge/ transmitter signature also can include signature information or signature identifiers sufficient to identify each badge and/or the person carrying or wearing the badge, such as by an employee number, patient code, or other suitable identifier. The lead 502 or drone dispensers 504 can further transmit this received information and information identifying the receiver such as a receiver identifier or other code identifying the area or location where the receiver is mounted or located, to the network 506 thereby allowing for processing including real time tracking, identifying, locating, and/or mapping of the movements or activities of selected persons throughout the particular facility. Although the present example discusses the use of one or more badges transmitting a plurality of signals 606 embodiments of the present disclosure are not limited thereto and may include tags, fobs, keycards, wristbands, or any other active or passive electronic device capable of being carried or worn.

In one embodiment, each badge 602 can include a body 602A with front 602B and side 602C surfaces, and one or more transmission devices 604. Such transmitters can include one or more IR transmitters 604, such as an LED or an array of LEDs, for transmitting a series of IR signals 606a-606e therefrom (FIGS. 10A-10B and 11); although other transmission devices/signals also can be used. In additional or alternative constructions, each badge 602 further can include a receiving device 608 configured to receive an activation signal for activating the badges 602. The badges 602 further can include control circuitry, e.g., a timer or clock module, resistors, transmission modules, etc., as well as a power source, such as one or more rechargeable or replaceable batteries or other suitable power source. FIGS. 10A-10B and 11 further indicate that each badge 602 can include a plurality of transmitters 604 disposed on various sides of the body 602a of the badge, such as two transmitters 604 on opposite side surfaces 602C (FIGS. 10A-10B and 11) and/or one or more transmitters 604 on a front surface 602B (FIGS. 10A and 11 and/or one or both side surfaces), facing in a forward direction (e.g., away from a person's chest) when the badge 602 is worn or carried by selected personnel. However, the transmitters 604 can be disposed or arranged in other configurations about the badge body 602A, and transmit signals in multiple directions without departing from the scope of the present disclosure.

In some embodiments, the badges 602 can be activated and begin transmitting signals 606A-E when a receiving device 608 thereof receives an initiation or activation signal from the lead 502 or one of the drone 504 dispensers. The receiving device may include an IR receiver, such as an IR receiving diode, photodiode, photocell, photo-emissive cell, photoconductive cell, photo-voltaic cell, photodetector, photosensor, light dependent resistor, light sensing circuit, or any other sensor for detecting electromagnetic signals. For example, when a person carrying or wearing a badge walks into a patient room or programmed or desired proximity, distance, range, or zone with respect to one or more of the lead 502 or drone 504 dispensers disposed throughout selected areas of a particular facility, such movement or infrared radiation emitted by the person(s) will be detected by the IR sensors thereof, causing the lead 502 or drone 504 dispensers to re-establish communication or connection with/to their power source, after which, the now-active lead and/or drone dispensers may periodically or substantially continuously transmit one or more activation or initiation signals (e.g., e.g., via the short-range transmitters/receivers 516A/516B and/or using the separate monitoring sensor assemblies 600A/B). When the badge 602 is positioned/located or moves within a predetermined distance, proximity, range, or zone of the one or more of lead 502 or drone 504 dispensers, the badge receiving device thereof 608 may receive, or otherwise detect, the activation or initiation signal and thereby activate or "wake up" the badge.

The intensities of the activation/initiation signals can be selected so that transmission of such signals is contained within, or limited to, prescribed areas of the selected facility to prevent erroneous activation of the badges 602. For instance, lead 502 or drone 504 dispensers or other activation devices can be positioned in a patient room (e.g., 560 in FIG. 9B) in a medical facility and can transmit activation signals at intensities that will only activate badges 602 carried by a medical professional when he or she walks or passes through an entryway to selected areas of the medical facility or within a certain distance, e.g., approximately 1 ft. to approximately 2 ft., into the patient room to thereby prevent erroneous activation or initiation of the badge 602 when the medical professional simply walks by or only initially enters the patient room.

When a receiver 608 of the badge 602 receives or otherwise detects an initiation/activation signal, the power source of the badge 602 can be activated and the badge 602 can begin transmission of signals 606a-606e. In some embodiments, the clock or timer module can be configured to operate so that the signals 606a-e are transmitted in a selected or programmed sequence one after the other for a predetermined time period (or at other intervals). For example, each transmission sequence or burst can last for a time period of approximately ms to approximately 10 ms with an intermission between each sequence of transmissions of approximately 0.1 ms to approximately 1 ms.

It further will be understood that other varying and/or longer or shorter sequence intervals and/or intermissions also can be used. By way of example, the signals can be transmitted in cycles with the weakest signal first 606a and the strongest signal last 606e; however, embodiments of the present disclosure are not limited to such sequence and the signals 606a-606e can be transmitted in the opposite sequence, i.e., with the strongest signal 606e first and the weakest signal 606e last and/or in any other sequence.

In addition, the badges 602 can reset the transmission of the signals after completion of a full sequence, such that the signals are transmitted in a periodic or substantially continuous cycle. Each badge 602 also can transmit signals 606a-606e in repeating cycles until the person carrying or wearing the badge 602 is no longer within the prerequisite proximity, distance, range or zone of one or more of the lead 502 or drone dispenser 504 such that the receiver 608 no longer detects or receives an initiation or activation signal, at which point the power source of the badge 602 can power down or the badge 602 can enter a low power mode or "sleep state."

Additionally, the badges 602 can be configured to produce a series of electrical signals or impulses for generating signals 606a-e, and each signal or electrical impulse can be modulated, controlled, or modified such that each signal 606a-e is transmitted with, or otherwise contains, signature information including a particular identifying code or unique signal identifier, such as a particular binary code decimal ("BCD"), alternative numeric signature, or any other identifier. For example, the power, amplitude, frequency, continuity, or other aspect or property of each signal can be modulated, modified, or controlled to generate the signature information, particular identifying code or unique signal identifier. The signals 606a-e also can include one or more components indicative of the signal strength/intensity of each transmitted signal, e.g., the identifying code signature identifier, and other components indicative of information corresponding to, or identifying each badge 602, which may include signature information or a signature identifier that may identify the person carrying each badge 602, with, for example, an employee id number, patient code, or other identifier. In addition, as shown in FIGS. 10A-10B and 11, each badge 602 further can be configured to transmit each of the signals 606a-e at a predetermined intensity/signal strength such that each signal can be received or detected at a predetermined distance, proximity, range, or zone and with a particular identifying code or unique signal identifier, such as BCDs: 0001, 0010, 0011, 0100, 0101.

In one embodiment, signal 606a can include identifying code or signal identifier 0001 and be transmitted at an strength or intensity such that it is received or detected within a distance, proximity, range, or zone of approximately 1 ft. radius around the badge 602; signal 606b can include identifying code or signal identifier 0010 and be transmitted at a strength or intensity such that it is received/detected within a distance, proximity, range, or zone of approximately 2 ft. radius; signal 606c can include a identifying code or signal identifier 0011 and be transmitted at a strength or intensity such that it is received/detected within a distance, proximity, range, or zone of approximately 3 ft. radius; signal 606d can include identifying code or signal identifier 0100 and be transmitted at a strength or intensity such that it is received/detected within a distance, proximity, range, or zone of approximately 4 ft. radius; and signal 606e can include a unique signal identifier 0101 and be transmitted at a strength or intensity such that it is received/detected within a distance, proximity, range, or zone of approximately 5 ft. radius. Though the present example embodiment is illustrated with five different signals with signal intensities/strengths varying at 1 ft. increments, any number of signals may be transmitted at any number of increments, including, but not limited to, one-four or a much greater number of signals, transmitted at increments of up to approximately 2-10 ft. or more or at much smaller intervals or increments such as approximately 10-5 in. or less.

In other embodiments, a substantially large number of signals can be transmitted from each badge 602 to improve the precision or accuracy of the detection of the distance, proximity, range, or zone in which the badge 602 can be received or detected. For example, up to approximately 100, up to approximately 1,000, up to approximately 10,000, up to approximately 100,000, or more signals varying with intensities can be transmitted from each badge 602. Transmitting such large numbers of signals can maintain a precise or accurate detection of the distance, range, proximity, or zone of the badges throughout continued use of the badges 602, such as through degradation of the components or at times of low battery power.

As discussed, the lead 502 and/or drone 504 dispensers can communication with the badges 602 using the short range transmitter/receivers 516A/516B and/or a separate monitoring sensor assembly 600A/B. In embodiments, the monitoring sensor assembly 600A/B of the lead 502 or drone 506 dispensers can include one or more receiving devices 610, such as an IR receiver, which can include IR receiving diodes, photodiodes, photocells, photo-emissive cells, photoconductive cells, photo-voltaic cells, semiconductor devices, photodetectors, photosensors, light dependent resistors, light sensing circuits, or any other sensor for detecting electromagnetic signals, configured to receive, or otherwise detect, signals 606a-e, as well as one or more transmission devices 612, which may include an IR transmitting LED, for activating or "waking up" the badges 602 (FIGS. 10B and 11). FIG. 11 further shows that that the monitoring sensor assembly 600A/B can include a plurality of receiving devices 610.

The monitoring sensor assembly 600A/B further will be in communication with the controller 510A/510B of the lead 502 or drone 504 dispensers. The controller 510A/510B can operate to control the transmitter receivers 516A/516B or the transmission devices 612 of the monitoring sensor assembly 600A/B to transmit an initiation or activation signal to activate or "wake up" the badges. The controller 510A/510B can also initially process/encode the signals 606a-e received or captured by the transmitter receivers 516A/516B or the receiving devices 610 of the monitoring sensor assembly 600A/B. For example, the controller 510A/510B can operate to interpolate information corresponding to the signal or signals 606a-e received and can identify the particular received signal based on its unique signal identifier, e.g. BCD 0001. After one or more signals are identified, the controller 510A/B can determine the approximate proximity, range, distance, or zone of the badge 602 to, or from, the lead 502 or drone 504 dispenser and also identity information corresponding to the person carrying or wearing badge 602, such as a medical professional's employee number, based on the unique signal identifier of each badge. Such information can be collected into records or packets that can be sent periodically, together with the primary receiver identifier, to the network 506, e.g., via the long range transmitter reliever 518A of the lead dispenser 502 (or optionally a long range transmitter receiver 518B of a drone dispenser 504).

For example, if the controller 510A/510B identifies or determines that the transmitter receivers 516A/516B or the receiving devices 610 of the monitoring sensor assembly 600A/B is only receiving one signal, i.e., signal 606e based on identifier 0001, the controller 510A/510B can determine that the badge 602 (and an individual wearing the badge 602) is approximately ft. away from the lead 502 or drone 504 dispenser. Alternatively, if controller 510A/510B identifies or determines that the transmitter receivers 516A/516B or the receiving devices 610 of the monitoring sensor assembly 600A/B is receiving all five of the signals 606a-e, based on identifiers 0001, 0010, 0011, 0100, 0101, the interpolation module can determine that the badge 602 (and a person wearing the badge) has moved approximately 1 ft. away from the lead 502 or drone 504 dispenser detecting those signals.

The controller 510A/510B further can send, or communicate, this information, e.g. the proximity, distance, or range of the badge 602 and an identifier of the person wearing or carrying the badge, to the network 506 for further processing using long range transmitter/receiver 518A/518B. The lead 502 or drone 504 dispensers also can transmit information identifying the dispenser, such as a dispenser identifier or other code corresponding to each lead or drone dispenser which may be indicative of a particular room, location, or area where the dispenser is located. Each dispenser 502/504 further can send collected records or data to the network 506. Each badge 602 again can have a unique ID signature, such as a BCD or other suitable identifier, and the lead 502 or drone 504 dispenser can decode each specific signature and send this information through the network 506 to a central monitoring system 614 where the data can be stored in a storage 616 (FIG. 7).

In some embodiments, when one or more signals are detected by one or more of the lead 502 or drone 504 dispensers, information corresponding to the signature information contained within the received signal identifying the badge or others unique identifier, and information identifying the dispensers 502/504 can be transmitted, in real time, to the network 506. This information, as well as any additional recorded information associated therewith, can then be transmitted to the central monitoring system 614. The central monitoring system 614 can include one or more servers, computers, smart phones, tablets, or other suitable computing devices 618. The computing devices will be in wireless or direct communication with the network 506 and generally will include one or more processors 620 with programming operable to perform processing of the information corresponding to the unique identifiers of each signal or series of signals received, such as tracking or measuring specific, predetermined, desirable or undesirable activities or movements or to detect the activation of lead 502 or drone 504 dispensers.

Accordingly, embodiments of the present disclosure can be used to track restaurant, food manufacturing, or medical employees' or patient's movements, location and activities throughout a predetermined space, for example, a patient room or an isolation ward. In one example, the lead 502 and drone 504 dispensers can be mounted, or otherwise disposed on, a door, cabinet, monitoring or other patient treatment equipment, and/or other suitable items, and the dispensers 502/504 can signal the central monitoring system 614 when activated. For example, the system 614 can detect when a restaurant employee enters a bathroom, and detect if and when that specific person activates a dispenser 502/504, or not, within a prescribed time period.

Additionally, the system 614 may include a database 622 connected to, or in communication with, the network 506 and/or the computing device 618, and the data stored in this database 622 may include information related to the patients checked into and/or medical professional workers working at a medical facility. For example, this data may include patient medical records, such as any communicable or infectious diseases/infections the patient has contracted, and the data may also include information relating to the time and date the patient checked into the medical facility, the duration of the patient's stay at the medical facility, the particular area, location, or room to which the patient is assigned and/or other medical facilities the patient has visited. This data may be organized in the database 622 based on a patient identification/tracking number which may include a patient's date of birth, Social Security number, or other identifier. As a result, the tracking records provided to the system 614 may be used to cross-reference received signal/tracking information including the location (e.g., the proximity, range, distance, or zone between a selected badge and one or more receivers) and identifier of the badges 602 and information, including the location and an identifier of one or more receivers with the information stored in the database 622 to track or map a particular person's movement through a medical facility and, based on such tracking or mapping, can potentially determine whether such person came in proximity to, or was otherwise exposed to, a particular infection or disease, such as staph, MERSA, Ebola, or other communicable infection or disease.

FIG. 11 shows an example embodiment of the present disclosure in which a lead 502 or drone 504 dispenser is disposed near the head of a patient's bed and/or at other locations such as on the wall behind the patient's bed, on the bedpost, or in a medical diagnostic device positioned near the head of the patient's bed. In this example, each badge 602, which can be worn or carried by a medical worker, can activate or "wake up" when the worker steps within a predetermined distance, proximity, range, or zone of the patient's bed and the badge 602 receives an activation or initiation signal from the dispenser 502/504, as described. In addition, or alternatively, one or more lead dispensers 502 or other activation devices can be disposed near an entryway, e.g., doorway 562, of the patent's room, such as on, or in, the doorframe, so that each badge 602 activates immediately when the medical worker carrying or wearing the badge enters the patient's room (FIG. 9B).

When the badge 602 is activated, the one or more transmitting devices 604 of the badge 602 can begin to transmit the series of signals 606a-e, and when, for example, the lead 502 or drone dispenser 504 receives one or more of the signals 606a-e, the dispenser 502/504 can indicate to the medical worker that a sanitation action is required. For example, the dispenser 502/504 can include a notification mechanism including one or more LEDs, or an alarm, that may illuminate, or sound, to indicate that a particular sanitation action is required. Additionally, the dispenser 502/504 may encode or capture the unique identifier identifying the particular worker contained within the signals 606a-e and may transmit, or otherwise communicate, the unique identifier and other information to the network 506. By way of example, the dispenser 502/504 may transmit the identifier of the worker and a receiver identify or other identifier identifying the particular dispenser 502/504, or receiver 610 of the plurality of receivers 610 in communication therewith, which received one or more of the transmitted signals from the badge(s) 602, and dispenser 502/504 may also transmit information corresponding to whether it was used or activated. This may allow for real time tracking of the specific location of the medical professional in relation to a particular patient or patients and compliance by the medical worker with the alerted sanitation action. This information, including the badge's/user's identifier, the primary receiver's identifier, and information on whether the sanitation device was activated, can further be stored in storage 616 for mapping of the particular patient visited and whether the medical worker complied with the alerted sanitation action.

In addition, embodiments of the present disclosure may provide for a determination of improved precision in tracing or mapping movements and/or an area or location(s) on or about the patient's body where the healthcare worker provided treatment or may have contacted the patient, since the worker's position with respect to the patient can be identified based on the particular signal or signals received, as described. By way of example, if a wall or bed mounted lead 502 or drone 504 dispenser identified with the patient receives only a first signal 606e, it can be determined that the medical worker wearing or carrying the badge came within a desired or predetermined proximity to the patient's feet or lower legs. If the lead 502 or drone 504 dispenser receives signals 606c, 606b, and 606a, it can be determined that the medical worker carrying or wearing the badge 602 is or was within a desired or predetermined proximity to the patient's torso, and if the lead 502 or drone 504 dispenser receives all signals 606a-e, it can be determined that the worker carrying or wearing the badge 602 is or was within a desired or predetermined proximity to the patient's head.

Records of the received signals or codes indicative of the detected location(s) of the medical worker in relation to the patient's body together with the badge identifier identifying the medical worker, can be collected and/or stored as records that can be transmitted, together with a unique code identifying the lead 502 or drone 504 dispenser that received and collected the record of these badge transmitted signals 606a-e to the network 506. Alternatively, a simple signal can be transmitted by each badge, and based upon a detected intensity or strength of signal thereof, as a result of its proximity to or distance from the lead 502 or drone 504 dispenser, can be monitored to determine and/or map locations of the badge wearer with respect to the patient's body. Additionally, each lead 502 or drone 504 dispenser may also measure the specific number or amount of time each of the signals 606a-e is received and encode these measurements and transmit them to the network 506.

Based on the unique code identifying the lead 502 or drone 504 dispenser providing each record received by the processor, the computing device 618 or lead 502 or drone 504 dispenser can identify the patient being treated and can then access the patient's medical history from the database 622 to determine whether a medical worker designated to provide a prescribed treatment to the patient has visited the patient or has yet to complete such a visit by cross-referencing whether the signal(s) received correspond to the designated worker, with the patient's medical information, and if so, monitor the duration of their visit and location(s) with respect to the patient's body can be used to substantiate/check their visit. For example, if the patient has an injury or a malady on his or her foot or lower leg, e.g., gangrene, this will be indicated in the patient's medical records stored in database 622, and it can be determined whether the designated medical worker both entered the patient's room and actually approached the patient and/or was in proximity to the injured area to an extent sufficient to provide requisite treatment thereto. As a further example, if the patient has an injury to their head, e.g., a blunt force trauma, and the identified badge/professional treating such an injury is detected by the lead 502 or drone 504 dispenser receiving a strength/intensity signal indicating they did not approach the patient's head, or all received signals are received for less than a required or expected duration for the medical worker to provide the requisite treatment for such a trauma, the computing device 618 or lead 502 or drone 504 dispenser can indicate/attach a note to such a record and/or call for a check/confirmation that the designated worker or another worker has provided the proper treatment to the patient.

Additionally, based on a detected location or locations of a healthcare worker, as identified by the signal or signals received and/or recorded from one or more identified primary receivers within the facility that have detected the worker's badge, the computing device 618 and/or the lead 502 or drone 504 dispenser can determine whether the healthcare worker was exposed to any communicable diseases or infections possessed by the patient, such as MRSA, staph, or Ebola, which may have been communicated to the healthcare worker. For example, if the patient possesses a communicable infection/disease on his or her foot and the medical worker comes within a certain proximity to the patient's foot (e.g., approximately 0.5 in to approximately 2 ft. or any other distance, range, or proximity sufficient to contract the infection/disease) it can be determined that the medical worker potentially was exposed to the communicable infection/disease by cross-referencing the signal received from the badge 602 of the medical worker, e.g., only signal 606e received, with the patient's health information or medical records indicating the communicable infection/disease on their foot.

Receipt of this signal information, in view of the known locations of the dispensers and receivers, can therefore allow for mapping of the movements and activities of the healthcare worker throughout the medical facility, including mapping or logging the particular communicable infections/diseases in which a particular healthcare worker encountered or was exposed to. Accordingly, real time tracking and mapping of all of the communicable diseases each person, e.g., healthcare workers or patients, in the facility has been exposed to can be achieved. Further, the computing device 616 and/or the lead 502 or drone 504 dispenser can generate forensic maps showing the particular positions of each of the persons in the medical facility, e.g., patients and healthcare workers, and the particular diseases or infections they were potentially exposed to and further store such maps in storage 616 (or storage 512A/B).

In embodiments, by cross-referencing the position of the healthcare worker based on the signal or signals received by the lead 502 or drone 504 dispenser and the health information or medical records of the patient, a particular sanitation action the healthcare worker is required to take can be determined and communicate such action to the health care worker. In this example, each badge worn by healthcare personnel (or the lead 502 or drone 504 dispensers) can include one or more altering or indication devices, which may include a series of LEDs, or an audible alarm, which can be a speaker(s) or other audio device, and the altering or indication devices can alert healthcare personnel to take particular sanitation actions, such as by executing a particular illumination sequence of the LEDs or sounding a predetermined number of tones with the alarm. Accordingly, based on a patient's particular health information stored in the database 622, including any communicable diseases or infections the patient may have, it can be determined what particular sanitation actions are required and transmit a signal containing information to the lead 502 or drone 504 dispenser receiving signals from one or more badges 602. In some embodiments, this information can then be relayed from the lead 502 or drone 504 dispenser to the badges 602 to activate a particular sequence, or specific color (e.g., red), of the LEDs or sound a specific tone or number of tones of the alarm to communicate whether, and which, sanitation action may be required.

For example, if a patient does not have a serious infection or disease, the processor can determine by cross-referencing the identified receivers located in the treatment area housing the patient and reporting contact with a monitored medical worker (i.e., by detector of their badge) with the patient's medical information stored on the database, and thereafter can transmit information to the lead 502 or drone 504 dispenser and/or to the badges 602 so that only a single LED may illuminate or only a signal tone may sound from the audible alarm, such as to indicate that minimal sanitation is required, e.g., washing hands or using hand sanitizer, and on the other hand, if the patient has a serious infection or disease, all of the LEDs on the badge 602 (or the lead 502 or drone 504 dispenser) may illuminate or produce a specific color or the alarm make sound numerous tones or a specific tone to indicate that a higher level of sanitation is required, e.g., changing of clothes, quarantine, or other disinfection procedure. The lead 502 or drone 504 dispenser, which may be coupled thereto, may also include a series of alerting/indication devices, such as LEDs or alarms that can light up in a particular sequence or with a particular color or make a series of sounds or tones to indicate various sanitations action required.

Additionally, if the medical worker does not take a particular sanitation action (e.g., does not activate or come within a certain proximity of a sanitation device) after coming within a particular area or zone, such as a zone or area with patients having a particular serious disease, the indicators on the badges or receivers can execute a particular LED illumination sequence or color or sound a distinct tone or number of tones to indicate a required sanitation action, e.g., change clothes or wash hands.

In a further example, the badges 602 may provide access to selected areas of a medical facility, e.g., patient rooms, such as by activating door locks coupled with RFID receivers. Accordingly, by cross-referencing the patient information or medical history of the patients in different areas of the medical facility with the identifier of, and other information relating to, the medical worker carrying or wearing the badge 602, it can be determined which workers should or should not be granted access to various areas of the facility to thereby ensure only properly trained or qualified medical personnel are allowed to enter various selected areas. In one example, the computing device 616 or the lead 502 or drone 504 dispensers can cross-reference medical information of patients in selected areas of the medical facility, including information on any infectious/communicable diseases the patient(s) may have contracted, in view of received information identifying the badge 602, which can also identify the medical working carrying such badge 602 and other information on the medical worker, which may also be stored in the database; and, can determine whether such identified medical professionals are permitted entry to the various selected areas of the medical facility based on this cross-referenced information. If a medical worker is determined not to be qualified to treat a particular disease or infection, such medical worker's badge 602 may not permit or grant them access into areas of the medical facility housing patients with such particular disease or infection.

In another example, access will only be granted to medical workers who have already taken the proper preparatory procedures to encounter patients with a specific infection or disease. For example, if a medical worker is required to put on a hazmat suit or other protective clothing or to take certain precautions/procedures prior to entering a patient area, detection of the medical worker's badge 602 may generate a signal to grant access to the particular area only after detecting the worker clears the required precautions, or alternatively, if a secondary badge linked to a receiver 3 of the hazmat suit or other protective clothing is detected. As another alternative, the medical worker may have to swipe, or hold their badge within a close proximity (approximately 0.5 in. to approximately 3 in.) to a receiver contained in the hazmat suit or other protective clothing. For example, the hazmat suit or other protective clothing may have one or more transmitting devices transmitting a code or identifier specific to each hazmat suit or other protective clothing, and the badge will not be permitted into the selected areas requiring such additional protection unless the signal from the badge is received along with a signal from the transmitter of the suit or protective clothing.

In a further aspect of the present disclosure, the lead 502 or drone 504 dispensers can track and identify equipment or personnel entering or passing through a series of predetermined zones or sub zones, the time the person identified with a certain badge 602/IR transmitter ID or signature remains in such zones and sub zones, and use or non-use of specific equipment in such zones or sub-zones. For instance, in medical facilities (drug rehab, nursing homes, hospitals, medical offices, etc.) personnel can be tracked in proximity to drug cabinets, hazardous areas, patient areas; and predetermined desirable or undesirable actions can be detected, such as cabinets/doors opening or closing, dispensers used or not used, equipment handled or not handled, areas approached or not approached. In each event detected and/or recorded, the data received by the computing device 616 or the lead 502 or drone 504 dispensers will be in real time and recorded for that specific signature. Multiple predetermined events according to the application and/or environment, e.g., hospital, food service, clean room, etc., in which the system is used, such as proximity to a dispenser and/or a receiver, use of a dispenser or a tool, and/or tracking through predetermined zones, can be read for each specific transmitter signature.

According to additional embodiments, which can include features that can be used with and/or incorporated into the above exemplary embodiments or that can replace various features of the above exemplary embodiments, embodiments of the present disclosure can be adapted for use as a tracking and proximity warning system for us in hospital patient rooms to help facilitate compliance with sanitizing and/or disinfection procedures and practices.

FIG. 9B illustrates operation of the IR subzone technology in one example embodiment set in hospital patient room 560. There are three dispensers 502/504, including a lead 502 and two drone 504 dispenser in this example showing the layout of a semi-private patient room 560 including two beds 564. Private or semi-private patient rooms are typical in most U.S. hospitals, but other countries frequently have multiple beds in a room. Depending on the size of the patient room, a minimum of two dispensers 504 can be positioned to track the presence of a healthcare provider proximate to beds 564; though any suitable number of dispensers such as three, four, or more dispensers can be employed. In the present example, each of the dispensers 502/504 can illuminate two subzones 630A/B that emanate from each dispenser 82a-c, and that receive infrared signals from badges 602 carried by various hospital personnel. However, embodiments of the present disclosure are not limited to two zones or subzones and only a single zone or more than two zones or subzones may be used for each dispenser.

As further shown in FIG. 9B, in a two bed-three dispenser scenario, the placement of the left drone dispenser 504 creates two subzones 630A/B, one of which (630B) provides coverage of the space to the left side of the first, left bed 564. The two subzones 630A/B created by right drone dispenser 504 cover the space to the right side of the first bed and to the left side of the second, right bed. An additional drone dispenser (not shown) further can be provided to create subzones to cover the space to the right side of the second bed 564. With this example, zone 630A for the left drone dispenser 630A and zone 630A for the right drone dispenser 504 are too far to the left from the first and second beds, respectively, to trigger an audio alarm or visual signal to a hospital worker when a hospital worker is at these beds, but any badge 602 detected in these zones will also be identified, tracked, and monitored. In order to fully utilize the IR subzone technology in a hospital environment, each healthcare worker or patient can carry or wear badges 602, which transmit signals with individualized signatures or other identifiers. The badges 602 can also respond illumination signals emitted by the dispensers 502/504. Subzones can allow for a determination of which hospital workers can into close proximity with which beds and the patients in the beds.

In a further exemplary embodiment, infrared technology can be combined with subzone technology to determine worker sanitation compliance utilizing one or more smart dispensers 502/504. As noted, the lead or drone dispensers 502/504 can, for example, generate a single IR source to create one or more IR dispenser subzones each having a unique address. Accordingly, any dispenser 502/504, can track or locate a worker, who can be carrying a badge 602 throughout a particular subzone location, and thus, each smart dispenser can track and monitor such worker's movement and activities throughout different subzones and/or determine the total time spent by the worker in each subzone.

Additionally, as discussed each badge 602 carried by workers can also utilize this subzone technology. For example, each badge 602 can generate a single IR source to create multiple IR badge subzones and each multiple IR badge subzone can have the same unique ID address. Further, the badges 602 can activate or wake up after entering any of the one or more IR dispenser subzones and transmit the unique badge ID to the dispenser and then go back to sleep. Accordingly, combining one or more IR dispenser subzones throughout a selected a work area with IR badge subzones can allow for identification and monitoring of the position and movements of a worker in real time to ensure compliance with sanitation requirements.

Figure 12B:
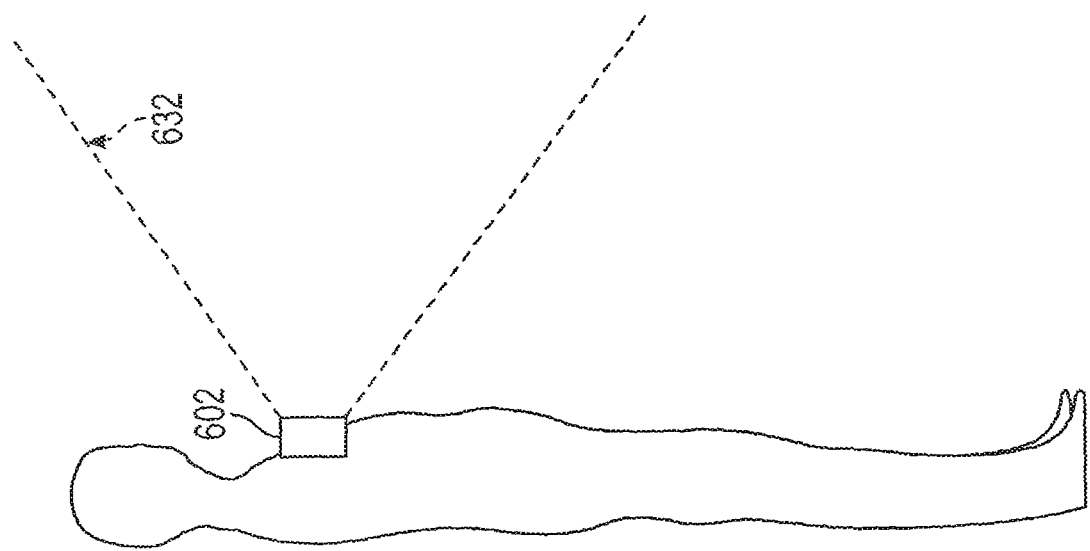
FIGS. 12A and 12B illustrate top and side views of a badge worn by personnel in the facility according to one aspect of the present disclosure.
Figure 12A:
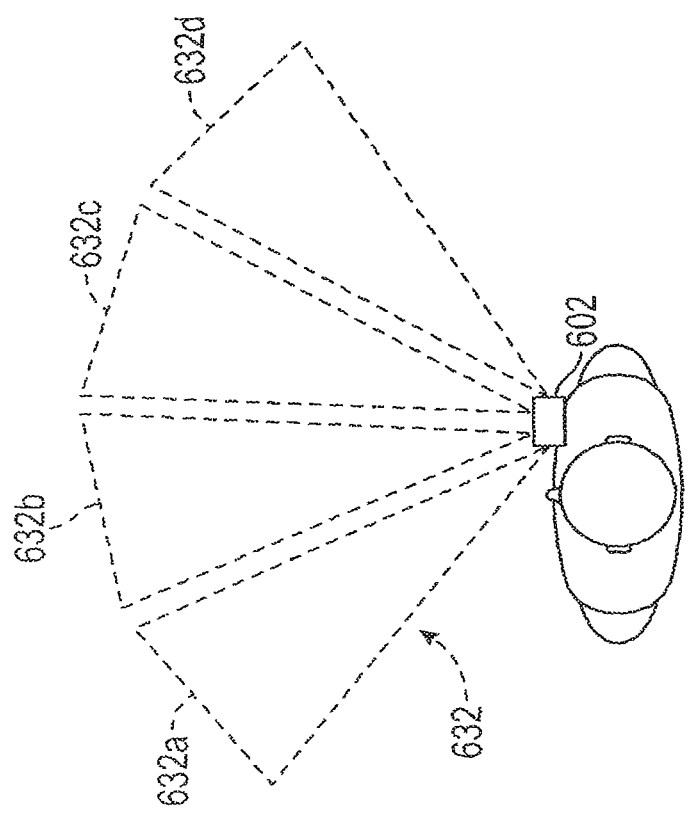

FIGS. 12A-B illustrate top and side views, respectively, for subzones 632 of badges 602 worn by such personnel or patients. FIG. 12A shows four subzones 632a-d that can be generated by the badges 602 receiving and responding to illumination emitted from a dispenser. The four subzones emanating from the primary badges 602 cover approximately 180 degrees horizontally from the healthcare worker. FIG. 12B indicates that the badges 602 may emit a signal that provides a significant amount of vertical coverage from the healthcare worker. The coverage provided both horizontally and vertically facilitates placement of the dispenser at various vertical positions along the room wall.

Figure 13:
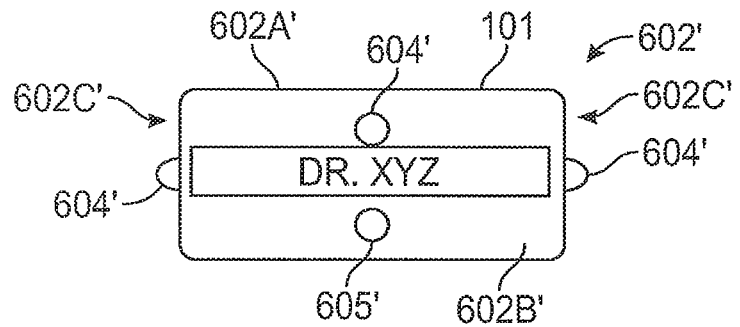
FIG. 13 illustrates a badge according to yet another aspect of the present disclosure.

In an additional or further alternative embodiment, the present disclosure provides an infrared identification tracking method and system for hospitals and/or food processing hygiene compliance. In this embodiment, each medical worker or healthcare professional can wear a badge 602', or badges 602', on their chest (FIG. 13). Each badge 602' can comprise, for example, at least three infrared LED's 604', in a configuration as shown of one LED in the front 602B' and one LED on each side 602C'. This configuration provides a coded person's identification and position within a predetermined zone. The predetermined zone can be designated by several factors, such as, distance, front, right, left side seen from the orientation of the badge 602'. The badge 602' may also include at least one infrared receiver 605' that functions to "wake up" the badge 602' when the badge receives a signal from a dispenser 502/504 or other tracking unit, such as those that are installed within a facility. Generally, the badge 602' can be in a ready state and can be woken up in order to provide for battery saving.

As shown in FIG. 13, each badge can include a badge body indicated at 602A', a center infrared LED indicated at 604', a right side LED indicated at 604', and a left side LED indicated at 604', and a wake-up infrared sensor indicated at 605'. The badge 604' shown in FIG. 13 also includes an identification (as shown, this badge belongs to "Dr. XYZ"). The compliance system then coordinates multiple hygiene dispensers installed in, for example, a patient's room. Additionally, for communication with the badges the monitoring sensor assembly 600 of each of the dispensers 502/504 generally comprises at least one infrared transmission LED, at least one front infrared receiver, at least one side infrared receiver, and at least one infrared sub-zone on at least one side of the unit. Still further, the facility can be provided with an exit room location tracking infrared relay or detector, which can be comprised of an IR receiver and an IR and/or RF transmitter. The signal can be sent when the person wearing the badge, generally a health care worker, leaves the patient's room, or any other location in the facility identifying the badge wearer's location.

Figure 14A:
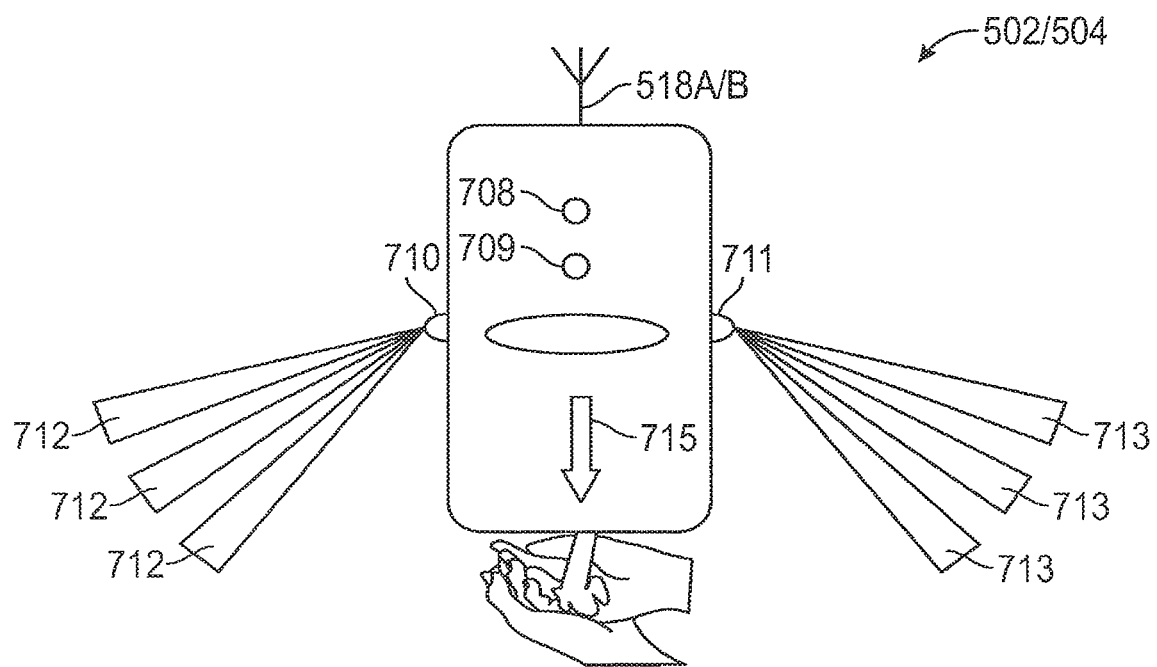
FIGS. 14A, 14B, and 14C illustrate a lead or drone dispensers including a monitoring sensor system that includes zone or side bar receivers.
Figure 14B:
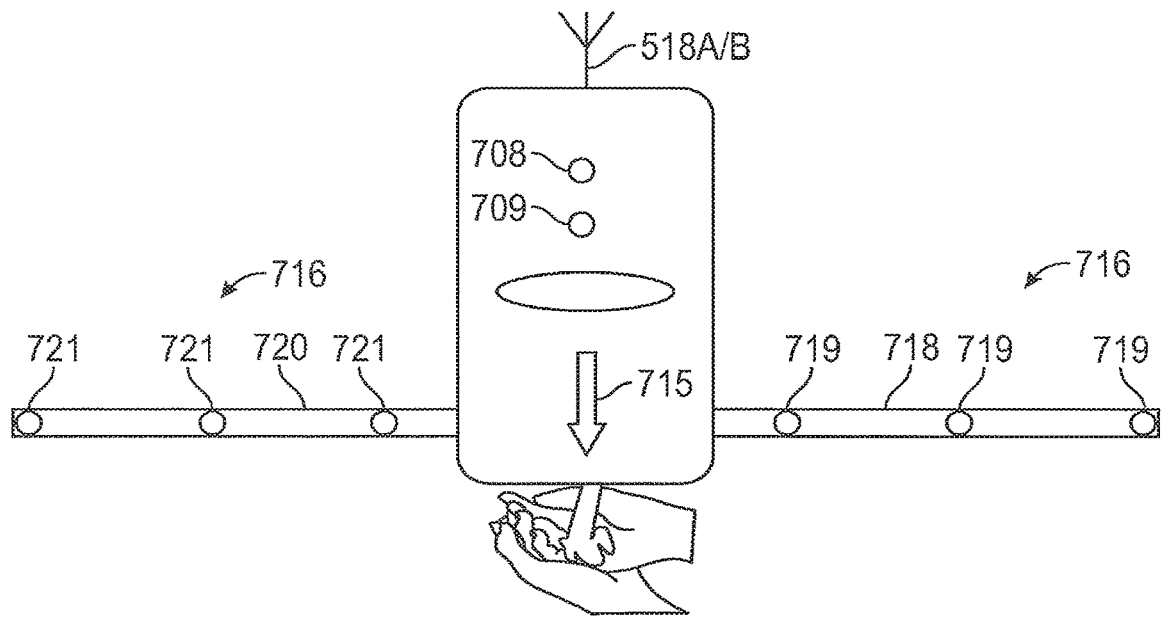
Figure 14C:
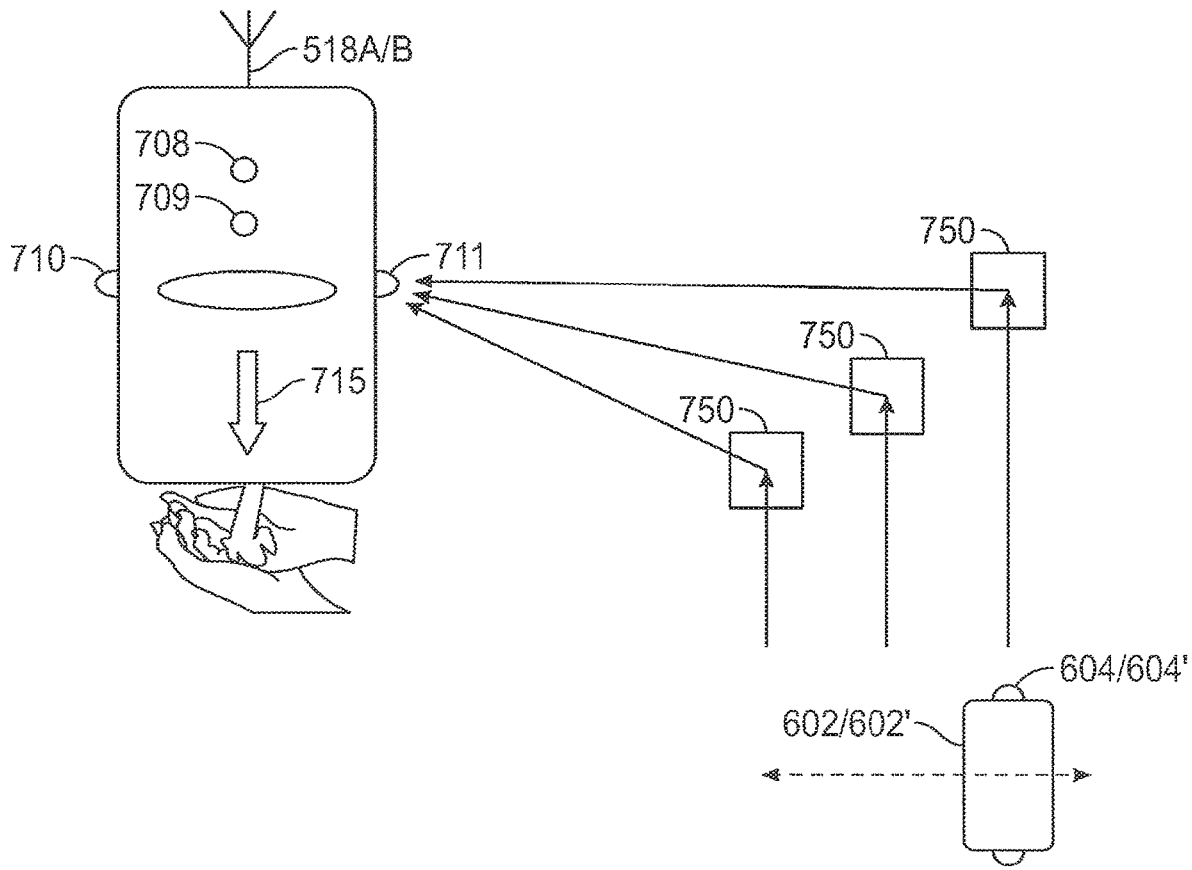

FIGS. 14A-14C illustrate various additional constructions for lead or drone dispensers 502/504 that can be positioned throughout the facility. The monitoring sensor assembly 600 of the dispenser 502/504 shown in FIG. 14A can include internal side subzone receivers 710/711. The monitoring sensor assembly 600 of the dispenser 502/504 further includes an infrared front receiver, generally indicated at 708, an infrared transmitter, generally indicated at 709, infrared left side receivers array (internal receivers), generally indicated at 710, infrared right side receivers array (internal receivers), generally indicated at 711. The internal side subzone receivers 710 generate infrared subzones, generally indicated at 712, and the infrared side subzone receivers 711 generate infrared subzones, generally indicated at 713. The dispenser 502/504 further can include a visual indicator 715, such as a blinking arrow as shown in FIG. 14A, that is activated when an individual wearing a badge 602 enters one of the subzones 712/713.

FIG. 14B shows a lead or drone dispenser 502/504 with side bar sub and zone receivers 716. As shown in FIG. 14BA, the dispenser 502/504 includes left sub zone bar 720, right sub zone bar 718, right infrared constant sensitivity sensors 719, and left infrared constant sensitivity sensors 721. FIG. 14C illustrates lead or drone dispenser 502/504 for detection of sub zones. For example, as shown in FIG. 14C, distance detection data can be achieved by replacing one of more of the IR receivers 719 of FIG. 14B with mirrors 750 that can be adjusted to reflect the received transmission from a badge's 602' respective transmitter 604' to the receivers 711/710, which are located on each side of the dispenser 502/504.

Additionally, devices, systems, etc. for mapping/tracking individuals throughout the facility are discussed in U.S. Pat. Nos. 9,741,233, 9,972,193, 10,446,013, which is specifically incorporated by reference herein as if set forth in its entirety.

The foregoing description generally illustrates and describes various embodiments of the present invention. It will, however, be understood by those skilled in the art that various changes and modifications can be made to the above-discussed construction of the present invention without departing from the spirit and scope of the invention as disclosed herein, and that it is intended that all matter contained in the above description or shown in the accompanying drawings shall be interpreted as being illustrative, and not to be taken in a limiting sense. Furthermore, the scope of the present disclosure shall be construed to cover various modifications, combinations, additions, alterations, etc., above and to the above-described embodiments, which shall be considered to be within the scope of the present invention. Accordingly, various features and characteristics of the present invention as discussed herein may be selectively interchanged and applied to other illustrated and non-illustrated embodiments of the invention, and numerous variations, modifications, and additions further can be made thereto without departing from the spirit and scope of the present invention as set forth in the appended claims.

The invention claimed is:

1. A dispensing and monitoring system for a facility, comprising:
 a plurality of dispensers, each comprising:
  at least one passive infrared radiation sensor configured to capture infrared radiation of one or more individuals; and
  a control system in communication with a power source and the at least one passive infrared radiation sensor, wherein the control system is configured to disconnect from the power source when the at least one passive infrared radiation sensor does not capture infrared radiation of one or more individuals, and to connect to the power source when the at least one passive infrared radiation sensor captures infrared radiation of one or more individuals,
 wherein each of the plurality of dispensers are positioned at selected locations about the facility, and wherein the control system thereof is configured to capture information related to movements and/or activities of individuals within the facility to facilitate monitoring movements and/or activities of the individuals throughout the facility;
 wherein the plurality of dispensers includes at least one lead dispenser and one or more drone dispensers in communication with the at least one lead dispenser and configured to communicate information captured thereby to the at least one lead dispenser;
 wherein the one or more drone dispensers is configured to transmit one or more alerts or notifications to the at least one lead dispenser if the one or more drone dispensers are experiencing an alert condition; and
 wherein a power source of the at least one lead dispenser remains connected to a control system of the at least one lead dispenser when a passive infrared radiation sensor of the lead dispenser or any of the one or more drone dispensers captures infrared radiation of one or more individuals.

2. The dispensing and monitoring system of claim 1, wherein monitoring of the movements and/or activities of the individuals throughout the facility comprises at least one of identifying, logging, mapping, and tracking movements and/or activities of the individuals throughout the facility.

3. The dispensing and monitoring system of claim 1, further comprising a plurality of badges carried by the individuals throughout the facility, each badge of the plurality of badges being configured to communicate with the plurality of dispensers to provide information monitoring movements of the individuals throughout the facility.

4. The dispensing and monitoring system of claim 3, wherein each badge of the plurality of badges includes a transmitter configured to transmit a plurality of signals, each of the signals including signature information identifying a corresponding badge from which each signal is sent and an identifying code for identifying each signal.

5. The dispensing and monitoring system of claim 4, wherein each signal of the plurality of signals is transmitted at a predetermined distance or at a predetermined signal strength, and wherein the control system of one or more dispensers of the plurality of dispensers is configured to determine a plurality of positions or movements of each badge in relation to the plurality of dispensers, based on the predetermined distance or signal strength of different signal of the plurality of signals received from each badge.

6. The dispensing and monitoring system of claim 3, wherein the facility comprises a medical facility further comprising at least one database configured to store information related to patients and the individuals moving throughout the medical facility, and wherein the dispensing and monitoring system is configured to cross-reference the information stored in the database with information monitoring the movements of the individuals within the facility.

7. The dispensing and monitoring system of claim 1, wherein one or more dispensers of the plurality of dispensers includes a long range transmitter/receiver that facilitates communication between the one or more dispensers and a network, wherein the one or more dispensers transmits captured information related to movements and/or activities of the individuals to the network with the long range transmitter/receiver.

8. The dispensing and monitoring system of claim 1, wherein one or more of the plurality of dispensers include a sheet material dispenser, and/or one or more of the plurality of dispensers include a liquid dispenser.

9. The dispensing and monitoring system of claim 1, wherein the at least one passive infrared radiation sensor is configured to capture infrared radiation of one or more individuals within a prescribed detection range, area, or zone covered by the at least one passive infrared radiation sensor.

10. The dispensing and monitoring system of claim 9, wherein the power source of the at least one lead dispenser is disconnected from the control system of the at least one lead dispenser when infrared radiation of one or more individuals is not detected within the prescribed detection range, area, or zone covered thereby and the at least one passive infrared radiation sensor of the lead dispenser or one or more drone dispensers for a selected time period.

11. The dispensing and monitoring system of claim 1, wherein the alert condition comprises at least one of an error condition, a low power condition, or a low supply condition.

12. A dispensing and monitoring system for a facility, comprising:
a plurality of dispensers positioned at selected locations about the facility, each dispenser comprising:
at least one passive infrared radiation sensor configured to capture infrared radiation of one or more individuals; and
a control system in communication with a power source and the at least one passive infrared radiation sensor, wherein the control system is configured to disconnect from the power source when the at least one passive infrared radiation sensor does not capture infrared radiation of one or more individuals, and to connect to the power source when the at least one passive infrared radiation sensor captures infrared radiation of one or more individuals;
wherein the plurality of dispensers includes at least one lead dispenser and one or more drone dispensers in communication with the at least one lead dispenser and configured to communicate information captured thereby to the at least one lead dispenser; and
wherein a power source of the at least one lead dispenser remains connected to a control system of the at least one lead dispenser when a passive infrared radiation sensor of the lead dispenser or any of the one or more drone dispensers captures infrared radiation of one or more individuals.

13. The dispensing and monitoring system of claim 12, wherein the control system thereof is configured to capture information related to movements and/or activities of individuals within the facility to facilitate monitoring movements and/or activities of the individuals throughout the facility.

14. The dispensing and monitoring system of claim 13, wherein monitoring of the movements and/or activities of the individuals throughout the facility comprises at least one of identifying, logging, mapping, and tracking movements and/or activities of the individuals throughout the facility.

15. The dispensing and monitoring system of claim 12, further comprising a plurality of badges carried by the individuals throughout the facility, each badge of the plurality of badges being configured to communicate with the plurality of dispensers to provide information monitoring movements of the individuals throughout the facility.

16. The dispensing and monitoring system of claim 15, wherein each badge of the plurality of badges includes a transmitter configured to transmit a plurality of signals, each of the signals including signature information identifying a corresponding badge from which each signal is sent and an identifying code for identifying each signal.

17. The dispensing and monitoring system of claim 16, wherein each signal of the plurality of signals is transmitted at a predetermined distance or at a predetermined signal strength, and wherein the control system of one or more dispensers of the plurality of dispensers is configured to determine a plurality of positions or movements of each badge in relation to the plurality of dispensers, based on the predetermined distance or signal strength of different signal of the plurality of signals received from each badge.

18. The dispensing and monitoring system of claim 15, wherein the facility comprises a medical facility further comprising at least one database configured to store information related to patients and the individuals moving throughout the medical facility, and wherein the dispensing and monitoring system is configured to cross-reference the information stored in the database with information monitoring the movements of the individuals within the facility.

19. The dispensing and monitoring system of claim 12, wherein one or more of the plurality of dispensers include a sheet material dispenser, and/or one or more of the plurality of dispensers include a liquid dispenser.

20. The dispensing and monitoring system of claim 12, wherein the at least one passive infrared radiation sensor is configured to capture infrared radiation of one or more individuals within a prescribed detection range, area, or zone covered by the at least one passive infrared radiation sensor.

21. The dispensing and monitoring system of claim 20, wherein the power source of the at least one lead dispenser is disconnected from the control system of the at least one lead dispenser when infrared radiation of one or more individuals is not detected within the prescribed detection range, area, or zone covered thereby and the at least one passive infrared radiation sensors of the lead dispenser or one or more drone dispensers for a selected time period.

22. The dispensing and monitoring system of claim 12, wherein the one or more drone dispensers configured to transmit one or more alerts or notifications to the at least one lead dispenser if the one or more drone dispensers are experiencing an alert condition.

23. The dispensing and monitoring system of claim 22, wherein the alert condition comprises at least one of an error condition, a low power condition, or a low supply condition.

24. A method of monitoring movement of individuals in a facility, comprising:
capturing infrared radiation emitted by one or more of individuals using at least one passive infrared radiation sensor of at least one dispenser of a plurality of dispensers located about the facility;

transmitting information from a set of drone dispensers of the plurality of dispensers to a lead dispenser of the plurality of dispensers;

monitoring movements and/or activities of each individual in relation to each dispenser that detects the individual;

connecting a control system of the lead dispenser with a power source when the at least one passive infrared radiation sensor of the lead dispenser or any of the drone dispensers captures infrared radiation of one or more individuals and disconnecting the control system of the lead dispenser from the power source of the lead dispenser when the at least one passive infrared radiation sensor of the lead dispenser or any of the drone dispensers does not capture infrared radiation of one or more individuals.

25. The method of claim 24, wherein monitoring of the movements and/or activities of the individuals throughout the facility comprises at least one of identifying, logging, mapping, and tracking movements and/or activities of the individuals throughout the facility.

26. The method of claim 25, further comprising:
transmitting one or more signals from a plurality of badges carried by the individuals throughout the facility; and
receiving the one or more signals at one or more of the plurality of dispensers to facilitate the identifying, mapping, and/or tracking of movements and/or activities of the individuals throughout the facility.

27. The method of claim 25, further comprising:
cross-referencing information related to the individuals stored in a database with information related to identified, mapped, and/or tracked movements and/or activities of the individuals.

28. The method of claim 24, wherein capturing infrared radiation includes capturing infrared radiation of one or more individuals within a prescribed detection range, area, or zone covered by the at least one passive infrared radiation sensor.

29. The method of claim 24, further comprising transmitting one or more alerts or notifications from the set of drone dispensers to the lead dispenser if the one or more drone dispensers are experiencing an alert condition.

30. The method of claim 29, wherein the alert condition comprises at least one of an error condition, a low power condition, or a low supply condition.

* * * * *